US009255070B2

(12) United States Patent
Ito et al.

(10) Patent No.: US 9,255,070 B2
(45) Date of Patent: Feb. 9, 2016

(54) METHOD OF DEUTERATION USING MIXED CATALYST

(75) Inventors: Nobuhiro Ito, Kawagoe (JP); Tsuneaki Maesawa, Kawagoe (JP); Kazushige Muto, Kawagoe (JP); Kosaku Hirota, Gifu (JP); Hironao Sajiki, Gifu (JP)

(73) Assignee: WAKO PURE CHEMICAL INDUSTRIES, LTD., Osaka (JP)

( * ) Notice: Subject to any disclaimer, the term of this patent is extended or adjusted under 35 U.S.C. 154(b) by 1338 days.

(21) Appl. No.: 10/585,629

(22) PCT Filed: Dec. 21, 2004

(86) PCT No.: PCT/JP2004/019049
§ 371 (c)(1),
(2), (4) Date: Jul. 11, 2006

(87) PCT Pub. No.: WO2005/070853
PCT Pub. Date: Aug. 4, 2005

(65) Prior Publication Data
US 2008/0234488 A1   Sep. 25, 2008

(30) Foreign Application Priority Data

Jan. 23, 2004  (JP) ................................. 2004-016075

(51) Int. Cl.
| C07D 213/74 | (2006.01) |
| C07B 59/00 | (2006.01) |
| C07C 37/00 | (2006.01) |
| C07C 51/353 | (2006.01) |
| C07C 209/68 | (2006.01) |
| C07D 213/80 | (2006.01) |

(52) U.S. Cl.
CPC .............. *C07D 213/74* (2013.01); *C07B 59/00* (2013.01); *C07C 37/00* (2013.01); *C07C 51/353* (2013.01); *C07C 209/68* (2013.01); *C07D 213/80* (2013.01); *C07B 2200/05* (2013.01)

(58) Field of Classification Search
USPC ............................ 562/493; 568/716; 564/305
See application file for complete search history.

(56) References Cited

U.S. PATENT DOCUMENTS

| 3,849,458 | A | 11/1974 | Dinh-Nguyen et al. |
| 4,591,626 | A | 5/1986 | Kawai et al. |
| 4,874,890 | A | 10/1989 | Kato et al. |
| 4,880,941 | A | 11/1989 | Shroot et al. |
| 5,221,768 | A | 6/1993 | Kato et al. |
| 5,830,763 | A | 11/1998 | Junk et al. |
| 6,794,522 | B2 | 9/2004 | Bergman et al. |
| 2005/0177015 | A1 | 8/2005 | Hirota et al. |
| 2006/0025596 | A1 | 2/2006 | Ito et al. |
| 2006/0116535 | A1 | 6/2006 | Ito et al. |

FOREIGN PATENT DOCUMENTS

| EP | 0 276 675 | 8/1988 |
| EP | 1 535 889 | 1/2005 |
| GB | 1103607 | 2/1968 |
| JP | 45-17402 | 6/1970 |
| JP | 47-12567 | 6/1972 |
| JP | 60-248666 | 12/1985 |
| JP | 61-275241 | 12/1986 |
| JP | 61-277648 | 12/1986 |
| JP | 62-56441 | 3/1987 |
| JP | 63-30435 | 2/1988 |
| JP | 63-30450 | 2/1988 |
| JP | 63-198638 | 8/1988 |
| JP | 5-19536 | 3/1993 |
| JP | 62-28014 | 8/1994 |
| WO | 03-104166 | 12/2003 |
| WO | 2004-011400 | 2/2004 |
| WO | 2004-046066 | 6/2004 |

OTHER PUBLICATIONS

Kalpala, J. et al Green Chemistry 2003, 5, 670-676.*
Kalpala et al Green Chemistry 2003, 5, 670-676.*
Kozo et al Bull. Chem. Soc. Japan 1962, 2, 228-232.*
Atkinson et al Canadian Journal of Chemistry 1967, 45, 1511-1518.*
Sajiki, Hironao et al: "Pd/C—H2-catalyzed deuterium exchange reaction of the benzylic site in D20" Synlett , (7), 1149-1151 Coden: Synles; ISSN: 0936-5214, 2002, XP002388047.
Rubottom, George M. et al: "Deuteration of pyridine derivatives: a very mild procedure" Tetrahedron , 46(15), 5055-64 Coden: Tetrab; ISSN: 0040-4020, 1990, XP002440716.
Sajiki, Hironao et al: "Efficient C—H/C-D Exchange Reaction on the Alkyl Side Chain of Aromatic Compounds Using Heterogeneous Pd/C in D20" Organic Letters , 6(9), 1485-1487 Coden: ORLEF7; ISSN: 1523-7060, 2004, XP00Z440717.
Fraser et al., "The Steric Effect in the Platinum-Catalyzed Exchange Reaction between Aromatic Ring Protons and Deuterium Oxide," Journal of the American Chemical Society, vol. 88, No. 19 (1966), p. 4365-4370.
Kirk-Othmer, Encyclopedia of Chemical Technology, 4$^{th}$ edition, vol. 5 (1993), p. 383-389.
Garnett et al., "Deuterium Exchange Reactions with Substituted Aromatics, II. The Monohalogenated Benzenes and Naphthalenes," Aust. J. Chem., vol. 14 (1961), p. 441-448.
Klei et al., "Iridium-Catalyzed H/D Exchange into Organic Compounds in Water," J. Am. Chem. Soc., vol. 24, No. 10, 2002, p. 2092-2093.
Hardacre et al., "A highly efficient synthetic procedure for deuterating imidazoles and imidazolium salts," Chem. Commun., 2001, p. 367-368.

(Continued)

*Primary Examiner* — Janet L Andres
*Assistant Examiner* — Daniel Carcanague
(74) *Attorney, Agent, or Firm* — Hamre, Schumann, Mueller & Larson, P.C.

(57) ABSTRACT

The subject of the present invention is to provide a method for deuteration, which can obtain a compound having an aromatic ring and/or a heterocyclic ring at an improved deuteration ratio. The present invention relates to a method for deuteration of a compound having an aromatic ring and/or a heterocyclic ring, comprising reacting the compound having an aromatic ring and/or a heterocyclic ring with a heavy hydrogen source in the presence of an activated mixed catalyst of not less than two kinds of catalysts selected from among a palladium catalyst, a platinum catalyst, a rhodium catalyst, an iridium catalyst, a ruthenium catalyst, a nickel catalyst and a cobalt catalyst.

17 Claims, No Drawings

(56) References Cited

OTHER PUBLICATIONS

Oba et al., "Biosynthesis of luciferin in the sea firefly, *Cypridina hilgendorfii*: L-tryptophan is a component in *Cypridina luciferin*," Tetrahedron Letters 43 (2002), p. 2389-2392.

Junk et al., "Hydrogen isotope exchange reactions involving C—H (D,T) bonds," Chemical Society Reviews, 1997, vol. 26, p. 401-406.

Garnett et al., "An NMR study of orientation effects in the catalytic deuteration and tritiation of aromatic compounds. Simplification of spin-coupled NMR spectra by the method of massive deuteration," Tetrahedron Letters, vol. 2, 1961, p. 516-522.

Elvidge et al., "Tritium nuclear magnetic resonance spectroscopy. Part 10. Distribution of Tritium in some labeled nitrogen heterocyclic compounds," J. Cheml Soc. Perkin Transactions 2, 1979, p. 386-388.

Kiuru et al., "Deuteration of Estrogens using Pd/C as a Catalyst," Synthesis and Applications of Isotropically Labelled Compounds 1997: Proceedings of the Sixth International Symposium, Philadelphia, USA, Sep. 14-18, 1997, (1998) p. 475-477.

Junk et al., "Preparative supercritical deuterium exchange in arenes and heteroarenes," Tetrahedron Letters v. 37, No. 20, (1996) p. 3445-3448.

Hsaio et al., "Preparation of Fully Deuterated Fatty Acids by Simple Method," American Oil Chemists' Society, Chicago, vol. 9, No. 11, p. 913-915 (1994).

Uno et al., "Infrared spectra of benzene- and pentadeuterobenzenesulfonyl compounds," Spectrochimica Acta, Part A: Molecular and Biomolecular Spectroscopy (1968), 24(11), p. 1705-12. (Abstract).

Wszolek et al., "Skeletal rearrangements in mass spectra. I. Bis-aryl compounds," Organic Mass Spectrometry (1968), 1(1), p. 127-37, (Abstract).

Usov et al., "Highly Mobile Solvent Holes in Viscous Squalane Solutions as Detected by Quantum Beats and MARY Spectroscopy Techniques," Journal of Physical Chemistry A (1999), 103(11), p. 1690. (Abstract).

Sokol'skii et al., "Selectivity during hydrogenation of phenylacetylene on metallic catalysts," Khimicheskaya (1987), (5), p. 32-35, (Abstract).

Tsuzuki et al., "Syntheses of phenol derivatives labeled with deuterium," Journal of Deuterium Science (1993), 3(1), p. 28-32. (Abstract).

Baker et al., "Aromatic Reactivity. Part XX, Diphenyl Sulphide, Dibenzofuran, and Dibenzothiophen in Detritiation," Chemical Abstracts (1961), 56, p. 5077-5081.

Werstiuk et al., "The High Temperature and Dilute Acid (HTDA) Procedure as a General Method of Replacing Aromatic Hydrogen by Deuterium. II," Canadian Journal of Chemistry (1974), 52, p. 2169-2171.

Usov et al., "Determination of a Fraction of a Spin-Correlated Radical Ion pairs in Irradiated Alkanes by Quantum Oscillation Technique," Radiation Physics and Chemistry (1997), 49, p. 237-243.

Search report for international application No. PCT/JP03/14182, dated Jan. 13, 2004 (4 pages).

Search report for international application No. PCT/JP03/14181, dated Jan. 13, 2004 (2 pages).

Search report for international application No. PCT/JP03/08783, dated Aug. 26, 2003 (3 pages).

Garnett, J.L. and Sollich, W.A., "Catalytic Deuterium Exchange Reactions with Aromatics VI. Studies in Platinum Catalyst Reproducibility and Activation Procedures," Journal of Catalysis, v. 2, p. 339-347 (1963).

Cristol, S. J. et al., "Bridged polycyclic compounds. XX. Cis stereochemistry of the addition of methanol and water to endo-trimethylenenorbornene," Tetrahedron Letters (1963), p. 185-9 (abstract).

\* cited by examiner

METHOD OF DEUTERATION USING MIXED CATALYST

TECHNICAL FIELD

The present invention relates to a method for deuteration of a compound having an aromatic ring and/or a heterocyclic ring, using an activated catalyst.

BACKGROUND OF THE INVENTION

A compound having a heavy hydrogen (deuterium and tritium) is said to be useful in various purposes. For example, a deuterated compound is very useful in elucidation of reaction mechanism and substance metabolism and used widely as a labeled compound. Said compound is also known to be useful as drugs, pesticides, organic EL materials, and the like due to change in stability and property of the compound itself by isotope effect thereof. A compound having tritium is also said to be useful as a labeled compound in animal tests and the like to survey absorption, distribution, concentration in blood, excretion, metabolism and the like of drugs, etc. Therefore, research on a compound having a heavy hydrogen (deuterium and tritium) has been recently increasing also in these fields.

Various methods for obtaining these deuterated compounds have conventionally been used. Among these methods, as a method for deuterating a compound having an aromatic ring or a heterocyclic ring, the present inventors developed a method for reacting a compound having an aromatic ring with heavy water in the presence of activated platinum carbon, and a method for reacting a compound having a heterocyclic ring with heavy water in the presence of activated palladium carbon or platinum carbon (Patent Document 1 and Patent Document 2).

Patent Document 1: International Publication No. WO2004/011400

Patent Document 2: International Publication No. WO2004/046066

DISCLOSURE OF THE INVENTION

Problem to be Solved by the Invention

The subject of the present invention is to provide a method for deuteration which can obtain a compound having an aromatic ring or a heterocyclic ring at an improved deuteration ratio.

Means to Solve the Problem

The present invention provides a method for deuteration of a compound having an aromatic ring and/or a heterocyclic ring, comprising reacting the compound having an aromatic ring and/or a heterocyclic ring with a heavy hydrogen source in the presence of an activated mixed catalyst of not less than two kinds of catalysts selected from among a palladium catalyst, a platinum catalyst, a rhodium catalyst, an iridium catalyst, a ruthenium catalyst, a nickel catalyst and a cobalt catalyst.

Effect of the Invention

The method for deuteration of the present invention can easily produce a compound having a high deuteration ratio for, for example, a hydrogen atom on an aromatic ring or a heterocyclic ring, a hydrogen atom belonging to an alkylene chain bonded to an aromatic ring or a heterocyclic ring and a hydrogen atom belonging to a substituent such as an alkylamino group. Particularly, the method for deuteration of the present invention can deuterate extremely efficiently a hydrogen atom at the ortho position on an aromatic ring to a substituent bonded to the aromatic ring and a hydrogen atom belonging to a carbon atom on a heterocyclic ring adjacent to a carbon atom bonded to a substituent on a heterocyclic ring, which has been said to be difficult to deuterate at a higher deuteration ratio by conventional methods.

BEST MODE FOR CARRYING-OUT OF THE INVENTION

In the present invention, a heavy hydrogen means deuterium (D) and tritium (T) and deuteration mean substitution with deuterium and tritium. Further, in the present specification, deuteration ratio means ratio of the amount of hydrogen atom substituted by a heavy hydrogen atom to the amount of hydrogen atom in a compound having an aromatic ring and/or a heterocyclic ring.

In a method for deuteration of the present invention, a compound having an aromatic ring may have not less than one hydrogen atom on the aromatic ring and includes, for example, an aromatic ring which may have a substituent.

An aromatic ring of the aromatic ring which may have a substituent may be a monocyclic ring or a condensation polycyclic ring, and in the case of a condensation polycyclic ring, two aromatic rings themselves or an aromatic ring and alicyclic ring may be condensed in a straight chained state, a branched state or a cyclic state, and such a condensation polycyclic ring to form a plane structure or a stereo structure.

Further, the number of substituent in the aromatic ring which may have a substituent is generally 1 to 5, preferably 1 to 2, and more preferably 1.

Specific examples of the above aromatic ring include, for example, benzene, naphthalene, anthracene, phenanthrene, 9,10-dihydroanthracene, naphthacene, pentaphene, pentacene, hexaphene, hexacene, heptaphene, heptacene, trinaphthylene, 1,4-dihydronaphthalene, pyrene, triphenylene, biphenylene, indene, indan, indacene, phenalene, fluorene, acenaphthene, acenaphthylene, fluoranthene, tetraphenylene, cholanethrene, acephenanthrylene, aceanthrylene, cyclopentaphenanthrene, chrysene, picene, pleiadene, rubicene, pyranthrene, coronene, perylene, rubrene, dibenzophenanthrene, 1,2-dibenzo-1,3-cycloheptadiene and ovalene. The substituents of the aromatic ring, which may have a substituent(s), include, for example, a halogen atom, a hydroxyl group, a mercapto group, an oxo group, a thioxo group, a carboxyl group, a sulfo group, a sulfino group, a sulfeno group, a phosphino group, a phosphinoyl group, a formyl group, an amino group, a cyano group and a nitro group, and the like, and further substituents, for example, an alkyl group, an alkenyl group, an aryl group, an aralkyl group, an alkoxy group, an aryloxy group, an alkylthio group, an arylthio group, an alkylsulfonyl group, an arylsulfonyl group, an alkylsulfinyl group, an arylsulfinyl group, an alkylphosphino group, an arylphosphino group, an alkylphosphinoyl group, an arylphosphinoyl group, an alkylamino group, an arylamino group, an alkoxycarbonyl group, an aryloxycarbonyl group, an alkoxysulfonyl group, an aryloxysulfonyl group, an acyl group, an acyloxy group, a sulfonyl group and a sulfonyloxy group, and the like, which may have a substituent(s), may be included.

The above alkyl group may be straight chained, branched or cyclic, and includes one generally having 1 to 20, preferably 1 to 15, more preferably 1 to 10 and further preferably 1 to 6 carbon atoms, which is specifically exemplified by a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a n-hexyl group, an isohexyl group, a sec-hexyl group, a tert-hexyl group, a neohexyl group, a 3-methylpentyl group, a 2-methylpentyl group, a 1,2-dimethylbutyl group, a n-heptyl group, an isoheptyl group, a sec-heptyl group, a tert-heptyl group, a neoheptyl group, an n-octyl group, an isooctyl group, a sec-octyl group, a tert-octyl group, a neooctyl group, a n-nonyl group, an isononyl group, a sec-nonyl group, a tert-nonyl group, a neononyl group, a n-decyl group, an isodecyl group, a sec-decyl group, a tert-decyl group, a neodecyl group, an undecyl group, a dodecyl group, a tridecyl group, a tetradecyl group, a pentadecyl group, a hexadecyl group, a heptadecyl group, an octadecyl group, a nonadecyl group, an icosyl group, a cyclopropyl group, a cyclopentyl group, a cyclohexyl group, a cycloheptyl group, a cyclooctyl group, a cyclononyl group, a cyclodecyl group, a cycloundecyl group, a cyclododecyl group, a cyclotridecyl group, a cyclotetradecyl group, a cyclopentadecyl group, a cyclohexadecyl group, a cycloheptadecyl group, a cyclooctadecyl group, a cyclononadecyl group and a cycloicosyl group.

The alkenyl group may be straight chained, branched or cyclic, and includes one generally having 2 to 20, preferably 2 to 10 and more preferably 2 to 6 carbon atoms, and having not less than 1 carbon-carbon double bond in the chain of the alkyl group having not less than 2 carbon atoms among the above alkyl groups, which is specifically exemplified by a vinyl group, an allyl group, a 1-propenyl group, an isopropenyl group, a 3-butenyl group, a 2-butenyl group, a 1-butenyl group, a 1,3-butadienyl group, a 4-pentenyl group, a 3-pentenyl group, a 2-pentenyl group, a 1-pentenyl group, a 1,3-pentadienyl group, a 2,4-pentadienyl group, a 1,1-dimethyl-2-propenyl group, an 1-ethyl-2-propenyl group, a 1,2-dimethyl-1-propenyl group, a 1-methyl-1-butenyl group, a 5-hexenyl group, a 4-hexenyl group, a 2-hexenyl group, a 1-hexenyl group, a 1-methyl-1-hexenyl group, a 2-methyl-2-hexenyl group, a 3-methyl-1,3-hexadienyl group, a 1-heptenyl group, an 2-octenyl group, a 3-nonenyl group, a 4-decenyl group, a 1-dodecenyl group, a 1-tetradecenyl group, a 1-hexadecenyl group, an 1-octadecenyl group, a 1-icosenyl group, a 1-cyclopropenyl group, a 2-cyclopentenyl group, a 2,4-cyclopentadienyl group, a 1-cyclohexenyl group, a 2-cyclohexenyl group, a 3-cyclohexenyl group, a 2-cycloheptenyl group, a 2-cyclononenyl group, a 3-cyclodecenyl group, a 2-cyclotridecenyl group, a 1-cyclohexadecenyl group, a 1-cyclooctadecenyl group and a 1-cycloicosenyl group.

The aryl group includes one generally having 6 to 14, preferably 6 to 10 carbon atoms, which is specifically exemplified by a phenyl group, a naphthyl group and an anthryl group.

The aralkyl group may be straight chained, branched or cyclic, and includes one generally having 7 to 34, preferably 7 to 20 and more preferably 7 to 15 carbon atoms, wherein a hydrogen atom in the above alkyl group is replaced by the above aryl group, which is specifically exemplified by a benzyl group, a phenylethyl group, a phenylpropyl group, a phenylbutyl group, a phenylpentyl group, a phenylhexyl group, a phenylheptyl group, a phenyloctyl group, a phenylnonyl group, a phenyldecyl group, a phenylundecyl group, a phenyldodecyl group, a phenyltridecyl group, a phenyltetradecyl group, a phenylpentadecyl group, a phenylhexadecyl group, a phenylheptadecyl group, a phenyloctadecyl group, a phenylnonadecyl group, a phenylicosyl group, a naphthylethyl group, a naphthylpropyl group, a naphthylbutyl group, a naphthylpentyl group, a naphthylhexyl group, a naphthylheptyl group, a naphthyloctyl group, a naphthylnonyl group, a naphthyldecyl group, a naphthylundecyl group, a naphthyldodecyl group, a naphthyltridecyl group, a naphthyltetradecyl group, a naphthylpentadecyl group, a naphthylhexadecyl group, a naphthylheptadecyl group, a naphthyloctadecyl group, a naphthylnonadecyl group, a naphthylicosyl group, an anthrylethyl group, an anthrylpropyl group, an anthrylbutyl group, an anthrylpentyl group, an anthrylhexyl group, an anthrylheptyl group, an anthryloctyl group, an anthrylnonyl group, an anthryldecyl group, an anthrylundecyl group, an anthryldodecyl group, an anthryltridecyl group, an anthryltetradecyl group, an anthrylpentadecyl group, an anthrylhexadecyl group, an anthrylheptadecyl group, an anthryloctadecyl group, an anthrylnonadecyl group, an anthrylicosyl group, a phenanthrylethyl group, a phenanthrylpropyl group, a phenanthrylbutyl group, a phenanthrylpentyl group, a phenanthrylhexyl group, a phenanthrylheptyl group, a phenanthryloctyl group, a phenanthrylnonyl group, a phenanthryldecyl group, a phenanthrylundecyl group, a phenanthryldodecyl group, a phenanthryltridecyl group, a phenanthryltetradecyl group, a phenanthrylpentadecyl group, a phenanthrylhexadecyl group, a phenanthrylheptadecyl group, a phenanthryloctadecyl group, a phenanthrylnonadecyl group and a phenanthrylicosyl group.

The alkoxy group may be straight chained, branched or cyclic, and includes one generally having 1 to 20, preferably 1 to 15, more preferably 1 to 10 and further preferably 1 to 6 carbon atoms, which is specifically exemplified by a methoxy group, an ethoxy group, a n-propoxy group, an isopropoxy group, a n-butoxy group, an isobutoxy group, a sec-butoxy group, a tert-butoxy group, a n-pentyloxy group, an isopentyloxy group, a sec-pentyloxy group, a tert-pentyloxy group, a neopentyloxy group, a n-hexyloxy group, an isohexyloxy group, a sec-hexyloxy group, a tert-hexyloxy group, a neohexyloxy group, a heptyloxy group, an octyloxy group, a nonyloxy group, a decyloxy group, an undecyloxy group, a tetradecyloxy group, a hexadecyloxy group, a heptadecyloxy group, a nonadecyloxy group, an icosyloxy group, a cyclohexyloxy group, a cyclooctyloxy group, a cyclodecyloxy group and a cyclononadecyloxy group.

The aryloxy group includes one generally having 6 to 14, preferably 6 to 10 carbon atoms, which is specifically exemplified by a phenoxy group, a naphthyloxy group and an anthryloxy group.

The alkylthio group may be straight chained, branched or cyclic, and includes one generally having 1 to 20, preferably 1 to 15, more preferably 1 to 10 and further preferably 1 to 6 carbon atoms, wherein an oxygen atom in the above alkoxy group is replaced by a sulfur atom, which is specifically exemplified by a methylthio group, an ethylthio group, a n-propylthio group, an isopropylthio group, a n-butylthio group, an isobutylthio group, a sec-butylthio, a tert-butylthio group, a n-pentylthio group, an isopentylthio group, a sec-pentylthio group, a tert-pentylthio group, a neopentylthio group, a n-hexylthio group, an isohexylthio group, a sec-hexylthio group, a tert-hexylthio group, a neohexylthio group, a heptylthio group, an octylthio group, a nonylthio group, a decylthio group, an undecylthio group, a dodecylthio group, a tridecylthio group, a tetradecylthio group, a pentadecylthio group, a hexadecylthio group, a heptadecylthio group, an octadecylthio group, a nonadecylthio group, an icosylthio group, a cyclohexylthio group, a cyclodecylthio group and a cycloheptadecylthio group.

The arylthio group includes one wherein an alkyl group in the above alkylthio group is replaced by the above aryl group, which is specifically exemplified by a phenylthio group, a naphthylthio group and an anthrylthio group.

The alkylsulfonyl group may be straight chained, branched or cyclic, and includes one generally having 1 to 20, preferably 1 to 15, more preferably 1 to 10 and further preferably 1 to 6 carbon atoms, which is specifically exemplified by a methylsulfonyl group, an ethylsulfonyl group, a n-propylsulfonyl group, an isopropylsulfonyl group, a n-butylsulfonyl group, an isobutylsulfonyl group, a sec-butylsulfonyl group, a tert-butylsulfonyl group, a n-pentylsulfonyl group, an isopentylsulfonyl group, a sec-pentylsulfonyl group, a tert-pentylsulfonyl group, a neopentylsulfonyl group, a n-hexylsulfonyl group, an isohexylsulfonyl group, a sec-hexylsulfonyl group, a tert-hexylsulfonyl group, a neohexylsulfonyl group, a heptylsulfonyl group, an octylsulfonyl group, a nonylsulfonyl group, a decylsulfonyl group, an undecylsulfonyl group, a tetradecylsulfonyl group, a hexadecylsulfonyl group, a heptadecylsulfonyl group, a nonadecylsulfonyl group, an icosylsulfonyl group, a cyclohexylsulfonyl group, a cyclooctylsulfonyl group, a cyclodecylsulfonyl group and a cyclononadecylsulfonyl group.

The arylsulfonyl group includes one generally having 6 to 14, preferably 6 to 10 carbon atoms, which is specifically exemplified by a phenylsulfonyl group, a naphthylsulfonyl group and an anthrylsulfonyl group.

The alkylsulfinyl group may be straight chained, branched or cyclic, and includes one generally having 1 to 20, preferably 1 to 15, more preferably 1 to 10 and further preferably 1 to 6 carbon atoms, which is specifically exemplified by a methylsulfinyl group, an ethylsulfinyl group, a n-propylsulfinyl group, an isopropylsulfinyl group, a n-butylsulfinyl group, an isobutylsulfinyl group, a sec-butylsulfinyl group, a tert-butylsulfinyl group, a n-pentylsulfinyl group, an isopentylsulfinyl group, a sec-pentylsulfinyl group, a tert-pentylsulfinyl group, a neopentylsulfinyl group, a n-hexylsulfinyl group, an isohexylsulfinyl group, a sec-hexylsulfinyl group, a tert-hexylsulfinyl group, a neohexylsulfinyl group, a heptylsulfinyl group, an octylsulfinyl group, a nonylsulfinyl group, a decylsulfinyl group, an undecylsulfinyl group, a dodecylsulfinyl group, a tridecylsulfinyl group, a tetradecylsulfinyl group, a pentadecylsulfinyl group, a hexadecylsulfinyl group, a heptadecylsulfinyl group, an octadecylsulfinyl group, a nonadecylsulfinyl group, an icosylsulfinyl group, a cyclohexylsulfinyl group, a cyclooctylsulfinyl group, a cyclodecylsulfinyl group and a cyclononadecylsulfinyl group.

The arylsulfinyl group includes one, wherein the alkyl group in the above alkylsulfinyl group is replaced by the above aryl group, which is specifically exemplified by a phenylsulfinyl group, a naphthylsulfinyl group and an anthrylsulfinyl group.

The alkylphosphino group includes one, wherein one or two of hydrogen atoms of a phosphino group are each independently replaced by the above alkyl group, which is specifically exemplified by a methylphosphino group, an ethylphosphino group, a n-propylphosphino group, an isopropylphosphino group, a n-butylphosphino group, an isobutylphosphino group, a tert-butylphosphino group, a pentylphosphino group, a hexylphosphino group, a heptylphosphino group, an octylphosphino group, a nonylphosphino group, a decylphosphino group, an undecylphosphino group, a dodecylphosphino group, a tridecylphosphino group, a tetradecylphosphino group, a pentadecylphosphino group, a hexadecylphosphino group, a heptadecylphosphino group, an octadecylphosphino group, a nonadecylphosphino group, an icosylphosphino group, a cyclopentylphosphino group, a cyclohexylphosphino group, a cycloheptylphosphino group, a dimethylphosphino group, an ethylmethylphosphino group, a diethylphosphino group, a methylpropylphosphino group, a dipropylphosphino group, an ethylhexylphosphino group, a dibutylphosphino group, a heptylmethylphosphino group, a methyloctylphosphino group, a decylmethylphosphino group, a dodecylethylphosphino group, a methylpentadecylphosphino group, an ethyloctadecylphosphino group, a cyclopentylmethylphosphino group, a cyclohexylmethylphosphino group, a cyclohexylethylphosphino group, a cyclohexylpropylphosphino group, a cyclohexylbutylphosphino group and a dicyclohexylphosphino group.

The arylphosphino group includes one, wherein one or two of hydrogen atoms of a phosphino group are each replaced by the above aryl group, which is specifically exemplified by a phenylphosphino group, a diphenylphosphino group, a naphthylphosphino group and an anthrylphosphino group.

The alkylphosphinoyl group includes one, wherein one or two of hydrogen atoms of a phosphinoyl group are each independently replaced by the above alkyl group, which is specifically exemplified by a methylphosphinoyl group, an ethylphosphinoyl group, a n-propylphosphinoyl group, an isopropylphosphinoyl group, a n-butylphosphinoyl group, an isobutylphosphinoyl group, a sec-butylphosphinoyl group, a tert-butylphosphinoyl group, a pentylphosphinoyl group, a hexylphosphinoyl group, a heptylphosphinoyl group, an octylphosphinoyl group, a nonylphosphinoyl group, a decylphosphinoyl group, an undecylphosphinoyl group, a dodecylphosphinoyl group, a tridecylphosphinoyl group, a tetradecylphosphinoyl group, a pentadecylphosphinoyl group, a hexadecylphosphinoyl group, a heptadecylphosphinoyl group, an octadecylphosphinoyl group, a nonadecylphosphinoyl group, an icosylphosphinoyl group, a cyclopentylphosphinoyl group, a cyclohexylphosphinoyl group, a cycloheptylphosphinoyl group, a dimethylphosphinoyl group, an ethylmethylphosphinoyl group, a diethylphosphinoyl group, a methylpropylphosphinoyl group, a dipropylphosphinoyl group, an ethylhexylphosphinoyl group, a dibutylphosphinoyl group, a heptylmethylphosphinoyl group, a methyloctylphosphinoyl group, a decylmethylphosphinoyl group, a dodecylethylphosphinoyl group, a methylpentadecylphosphinoyl group, an ethyloctadecylphosphinoyl group, a cyclopentylmethylphosphinoyl group, a cyclohexylmethylphosphinoyl group, a cyclohexylethylphosphinoyl group, a cyclohexylpropylphosphinoyl group, a cyclohexylbutylphosphinoyl group and a dicyclohexylphosphinoyl group.

The arylphosphinoyl group includes one, wherein one or two of hydrogen atoms of a phosphinoyl group are replaced by the above aryl group, which is specifically exemplified by a phenylphosphinoyl group, a diphenylphosphinoyl group, a naphthylphosphinoyl group and an anthrylphophinoyl group.

The alkylamino group includes one, wherein one or two of hydrogen atoms of an amino group are each independently replaced by the above alkyl group, which is specifically exemplified by a methylamino group, an ethylamino group, a n-propylamino group, an isopropylamino group, a n-butylamino group, an isobutylamino group, a sec-butylamino group, a tert-butylamino group, a pentylamino group, a hexylamino group, a heptylamino group, an octylamino group, a nonylamino group, a decylamino group, an undecylamino group, a dodecylamino group, a tridecylamino group, a tetradecylamino group, a pentadecylamino group, a hexadecylamino group, a heptadecylamino group, an octadecylamino group, a nonadecylamino group, an icosylamino group, a cyclopentylamino group, a cyclohexylamino group, a cycloheptylamino group, a dimethylamino group, an ethylmethylamino group, a diethylamino group, a methylpropylamino group, a dipropylamino group, an ethylhexylamino group, a dibutylamino group, a heptylmethylamino group, a methyloctylamino group, a decylmethylamino group, a dodecylethylamino group, a methylpentadecylamino group, an ethyloctadecylamino group, a cyclopentylmethylamino group, a cyclohexylmethylamino group, a cyclohexylethylamino group, a cyclohexylpropylamino group, a cyclohexylbutylamino group and a dicyclohexylamino group.

The arylamino group includes one, wherein one or two of hydrogen atoms of an amino group are replaced by the above aryl group, which is specifically exemplified by a phenylamino group, a diphenylamino group, a naphthylamino group and an anthrylamino group.

The alkoxycarbonyl group may be straight chained, branched or cyclic, and includes one generally having 2 to 21, preferably 2 to 15, more preferably 2 to 10 and further preferably 2 to 6 carbon atoms, and having further a carbonyl group bonded to an oxygen atom of the above alkoxy group, which is specifically exemplified by a methoxycarbonyl group, an ethoxycarbonyl group, a n-propoxycarbonyl group, an isopropoxycarbonyl group, a n-butoxycarbonyl group, an isobutoxycarbonyl group, a sec-butoxycarbonyl group, a tert-butoxycarbonyl group, a n-pentyloxycarbonyl group, an isopentyloxycarbonyl group, a sec-pentyloxycarbonyl group, a tert-pentyloxycarbonyl group, a neopentyloxycarbonyl group, a hexyloxycarbonyl group, a cyclohexyloxycarbonyl group, a heptyloxycarbonyl group, a cycloheptyloxycarbonyl group, an octyloxycarbonyl group, a nonyloxycarbonyl group, a decyloxycarbonyl group, a cyclodecyloxycarbonyl group, an undecyloxycarbonyl group, a tridecyloxycarbonyl group, a tetradecyloxycarbonyl group, a pentadecyloxycarbonyl group, a hexadecyloxycarbonyl group, a heptadecyloxycarbonyl group, a cycloheptadecyloxycarbonyl group, an octadecyloxycarbonyl group, a nonadecyloxycarbonyl group, an icosyloxycarbonyl group, a cyclopentyloxycarbonyl group, a cyclohexyloxycarbonyl group and a cyclooctyloxycarbonyl group.

The aryloxycarbonyl group includes one generally having 7 to 15, preferably 7 to 11 carbon atoms, which is specifically exemplified by a phenyloxycarbonyl group, a naphthyloxycarbonyl group and an anthryloxycarbonyl group.

The alkoxysulfonyl group may be straight chained, branched or cyclic, and includes one generally having 2 to 21, preferably 2 to 15, more preferably 2 to 10 and further preferably 2 to 6 carbon atoms, having further a sulfonyl group bonded to an oxygen atom of the above alkoxy group, which is specifically exemplified by a methoxysulfonyl group, an ethoxysulfonyl group, a n-propoxysulfonyl group, an isopropoxysulfonyl group, a n-butoxysulfonyl group, an isobutoxysulfonyl group, a sec-butoxysulfonyl group, a tert-butoxysulfonyl group, a n-pentyloxysulfonyl group, an isopentyloxysulfonyl group, a sec-pentyloxysulfonyl group, a tert-pentyloxysulfonyl group, a neopentyloxysulfonyl group, a hexyloxysulfonyl group, a cyclohexyloxysulfonyl group, a heptyloxysulfonyl group, a cycloheptyloxysulfonyl group, an octyloxysulfonyl group, a nonyloxysulfonyl group, a decyloxysulfonyl group, a cyclodecyloxysulfonyl group, an undecyloxysulfonyl group, a dodecyloxysulfonyl group, a tridecyloxysulfonyl group, a tetradecyloxysulfonyl group, a pentadecyloxysulfonyl group, a hexadecyloxysulfonyl group, a heptadecyloxysulfonyl group, a cycloheptadecyloxysulfonyl group, an octadecyloxysulfonyl group, a nonadecyloxysulfonyl group, an icosyloxysulfonyl group, a cyclopentyloxysulfonyl group, a cyclooctyloxysulfonyl group and a cycloheptadecyloxysulfonyl group.

The aryloxysulfonyl group includes one generally having 7 to 15, preferably 7 to 11 carbon atoms, which is specifically exemplified by a phenyloxysulfonyl group, a naphthyloxysulfonyl group and an anthryloxysulfonyl group.

The acyl group includes one derived from an aliphatic carboxylic acid and an aromatic carboxylic acid.

The acyl group derived from an aliphatic carboxylic acid may be straight chained, branched or cyclic, and may also have a double bond in the chain, and includes one generally having 2 to 20, preferably 2 to 15, more preferably 2 to 10 and further preferably 2 to 6 carbon atoms, which is specifically exemplified by an acetyl group, a propionyl group, a butyryl group, an isobutyryl group, a valeryl group, an isovaleryl group, a pivaloyl group, a hexanoyl group, a heptanoyl group, an octanoyl group, a decanoyl group, a lauroyl group, a myristoyl group, a palmitoyl group, a stearoyl group, an icosanoyl group, an acryloyl group, a methacryloyl group, a crotonoyl group and an oleoyl group.

The acyl group derived from an aromatic carboxylic acid includes one generally having 7 to 15, preferably 7 to 11 carbon atoms, which is specifically exemplified by a benzoyl group, a naphthoyl group and an anthroyl group.

The acyloxy group includes one derived from a carboxylic acid and having further an —O— bonded to the above acyl group derived from a carboxylic acid, which is exemplified by an acyloxy group derived from an aliphatic carboxylic acid and an aromatic carboxylic acid.

The acyloxy group derived from an aliphatic carboxylic acid may be straight chained, branched or cyclic and may have further a double bond in the chain, and includes one generally having 2 to 20, preferably 2 to 15, more preferably 2 to 10 and further preferably 2 to 6 carbon atoms, which is specifically exemplified by an acetyloxy group, a propionyloxy group, a butyryloxy group, an isobutyryloxy group, a valeryloxy group, an isovaleryloxy group, a pivaloyloxy group, a hexanoyloxy group, a heptanoyloxy group, an octanoyloxy group, a decanoyloxy group, a lauroyloxy group, a myristoyloxy group, a palmitoyloxy group, a stearoyloxy group, an icosanoyloxy group, an acryloyloxy group, a methacryloyloxy group, a crotonoyloxy group, an oleoyloxy group, a cyclohexanoyloxy group and a cyclodecanoyloxy group.

The acyloxy group derived from an aromatic carboxylic acid includes one generally having 7 to 15, preferably 7 to 11 carbon atoms, which is specifically exemplified by a benzoyloxy group, a naphthoyloxy group and an anthroyloxy group.

The sulfonyl group includes one derived from an aliphatic sulfonic acid and an aromatic sulfonic acid.

The sulfonyl group derived from an aliphatic sulfonic acid may be straight chained, branched or cyclic, and includes one generally having 1 to 20, preferably 1 to 15, more preferably 1 to 10 and further preferably 1 to 6 carbon atoms, which is specifically exemplified by a methylsulfonyl group, an ethylsulfonyl group, a n-propylsulfonyl group, an isopropylsulfonyl group, a n-butylsulfonyl group, an isobutylsulfonyl group, a sec-butylsulfonyl group, a tert-butylsulfonyl group, a pentylsulfonyl group, a hexylsulfonyl group, a heptylsulfonyl group, an octylsulfonyl group, a nonylsulfonyl group, a decylsulfonyl group, an undecylsulfonyl group, a dodecylsulfonyl group, s tridecylsulfonyl group, a tetradecylsulfonyl group, a pentadecylsulfonyl group, a hexadecylsulfonyl group, a heptadecylsulfonyl group, an octadecylsulfonyl group, a nonadecylsulfonyl group, an icosylsulfonyl group, a cyclohexylsulfonyl group and a cyclodecylsulfonyl group.

The sulfonyl group derived from an aromatic sulfonic acid includes one generally having 6 to 14, preferably 6 to 10 carbon atoms, which is specifically exemplified by a phenylsulfonyl group, a naphthylsulfonyl group and an anthrylsulfonyl group.

The sulfonyloxy group includes one derived from a sulfonic acid and having further an —O— bonded to the above sulfonyl group derived from a sulfonyl acid, which is exemplified by a sulfonyloxy group derived from an aliphatic sulfonic acid and an aromatic sulfonic acid.

The sulfonyloxy group derived from an aliphatic sulfonic acid may be straight chained, branched or cyclic, and includes one generally having 1 to 20, preferably 1 to 15, more preferably 1 to 10 and further preferably 1 to 6 carbon atoms, which is specifically exemplified by a methylsulfonyloxy group, an ethylsulfonyloxy group, a n-propylsulfonyloxy group, an isopropylsulfonyloxy group, a n-butylsulfonyloxy group, an isobutylsulfonyloxy group, a sec-butylsulfonyloxy group, a tert-butylsulfonyloxy group, a pentylsulfonyloxy group, a hexylsulfonyloxy group, a heptylsulfonyloxy group, an octylsulfonyloxy group, a nonylsulfonyloxy group, a decylsulfonyloxy group, an undecylsulfonyloxy group, a dodecylsulfonyloxy group, a tridecylsulfonyloxy group, a tetradecylsulfonyloxy group, a pentadecylsulfonyloxy group, a hexadecylsulfonyloxy group, a heptadecylsulfonyloxy group, an octadecylsulfonyloxy group, a nonadecylsulfonyloxy group, an icosylsulfonyloxy group, a cyclopentylsulfonyloxy group and a cyclohexylsulfonyloxy group.

The sulfonyloxy group derived from an aromatic sulfonic acid includes one generally having 6 to 14, preferably 6 to 10 carbon atoms, which is specifically exemplified by a phenylsulfonyloxy group, a naphthylsulfonyloxy group and an anthrylsulfonyloxy group.

The halogen atom includes, for example, a chlorine atom, a bromine atom, a fluorine atom and an iodine atom, and among others, a chlorine atom is preferable.

The carboxyl group, the sulfo group, the sulfino group, the sulfeno group, the phosphino group and the phosphinoyl group include also one, wherein a hydrogen atom in these groups is replaced by an alkali metal atom such as sodium, potassium and lithium.

The substituent of an aromatic ring which may have a substituent relating to the present invention, that is the above alkyl group, alkenyl group, aryl group, aralkyl group, alkoxy group, aryloxy group, alkylthio group, arylthio group, alkylsulfonyl group, arylsulfonyl group, alkylsulfinyl group, arylsulfinyl group, alkylphosphino group, arylphosphino group, alkylphosphinoyl group, arylphosphinoyl group, alkylamino group, arylamino group, alkoxycarbonyl group, aryloxycarbonyl group, alkoxysulfonyl group, aryloxysulfonyl group, acyl group and acyloxy group, may further have a substituent including, for example, an alkyl group, an alkenyl group, an alkynyl group, an aryl group, a hydroxyl group, an alkoxy group, an amino group, an alkylamino group, a mercapto group, an alkylthio group, an formyl group, an acyl group, a carboxyl group, an alkoxycarbonyl group, a carbamoyl group and an alkylcarbamoyl group, and these substituents may be present in number of generally 1 to 6, preferably 1 to 4, more preferably 1 to 2 in the substituent of an aromatic ring.

The substituent of the substituent of an aromatic ring relating to the present invention, that is an alkyl group, an alkenyl group, an aryl group, an alkoxy group, an alkylamino group, an alkylthio group, an acyl group, a carboxyl group and an alkoxycarbonyl group, includes the same one as the above substituent of an aromatic ring.

The alkynyl group as the substituent of the substituent of an aromatic ring relating to the present invention, may be straight chained, branched or cyclic, and includes one generally having 2 to 20, preferably 2 to 10 and more preferably 2 to 6 carbon atoms, and having not less than one carbon-carbon triple bond in the chain of an alkyl group having not less than 2 carbon atoms among the above alkyl groups, which is specifically exemplified by an ethenyl group, a 2-propynyl group, a 2-pentynyl group, a 2-nonyl-3-butynyl group, a cyclohexyl-3-ynyl group, a 4-octynyl group and 1-methyldecyl-5-ynyl group.

The alkylcarbamoyl group as the substituent of the substituent of an aromatic ring relating to the present invention, includes one, wherein one or two of hydrogen atoms of a carbamoyl group are each independently replaced by the above alkyl group, which is specifically exemplified by a methylcarbamoyl group, an ethylcarbamoyl group, a n-propylcarbamoyl group, an isopropylcarbamoyl group, a n-butylcarbamoyl group, an isobutylcarbamoyl group, a sec-butylcarbamoyl group, a tert-butylcarbamoyl group, a pentylcarbamoyl group, a hexylcarbamoyl group, a heptylcarbamoyl group, an octylcarbamoyl group, a nonylcarbamoyl group, a decylcarbamoyl group, an undecylcarbamoyl group, a dodecylcarbamoyl group, a tridecylcarbamoyl group, a tetradecylcarbamoyl group, a pentadecylcarbamoyl group, a hexadecylcarbamoyl group, a heptadecylcarbamoyl group, an octadecylcarbamoyl group, a nonadecylcarbamoyl group, an icosylcarbamoyl group, a cyclopentylcarbamoyl group, a cyclohexylcarbamoyl group, a cycloheptylcarbamoyl group, a dimethylcarbamoyl group, an ethylmethylcarbamoyl group, a diethylcarbamoyl group, a methylpropylcarbamoyl group, a dipropylcarbamoyl group, an ethylhexylcarbamoyl group, a dibutylcarbamoyl group, a heptylmethylcarbamoyl group, a methyloctylcarbamoyl group, a decylmethylcarbamoyl group, a dodecylethylcarbamoyl group, a methylpentadecylcarbamoyl group, an ethyloctadecylcarbamoyl group, a cyclopentylmethylcarbamoyl group, a cyclohexylmethylcarbamoyl group, a cyclohexylethylcarbamoyl group, a cyclohexylpropylcarbamoyl group, a cyclohexylbutylcarbamoyl group and a dicyclohexylcarbamoyl group.

In a method for deuteration of the present invention, a compound having a heterocyclic ring includes one having a heterocyclic ring containing not less than 1 hetero atom, preferably 1 to 3 hetero atoms and not less than 1 hydrogen atom present on said heterocyclic ring.

The hetero atom contained in a heterocyclic ring includes generally a nitrogen atom, an oxygen atom and a sulfur atom, and among others, a nitrogen atom is preferable.

The above heterocyclic ring includes a generally 3- to 20-membered, preferably 3- to 14-membered, more preferably 5- to 10-membered monocyclic heterocyclic ring or polycyclic heterocyclic ring, which may have aromatic properties. Further, the heterocyclic ring is, in the case of a monocyclic heterocyclic ring, more preferably 5- to 6-membered, and in the case of a polycyclic heterocyclic ring, more preferably 9- to 10-membered and particularly preferably 9-membered. These heterocyclic rings may be condensed in straight chained state, branched state or cyclic state and may take a plane structure or a stereo structure.

Further, said heterocyclic ring may have generally 1 to 5, preferably 1 to 2, more preferably 1 substituent.

Specific examples of the monocyclic heterocyclic ring include, for example, 3-membered heterocyclic rings having 1 hetero atom such as an oxirane ring and an aziridine ring; 5-membered heterocyclic rings having 1 hetero atom such as a furan ring, a thiophene ring, a pyrrole ring, a 2H-pyrrole ring, a pyrroline ring, a 2-pyrroline ring and a pyrrolidine ring; 5-membered heterocyclic rings having 2 hetero atoms such as a 1,3-dioxolan ring, an oxazole ring, an isooxazole ring, an 1,3-oxazole ring, a thiazole ring, an isothiazole ring, a 1,3-thiazole ring, an imidazole ring, an imidazoline ring, an 2-imidazoline ring, an imidazolidine ring, a pyrazole ring, a pyrazoline ring, a 3-pyrazoline ring and a pyrazolidine ring; 5-membered heterocyclic rings having 3 hetero atoms such as a furazan ring, a triazole ring, a thiadiazole ring and an oxadiazole ring; 6-membered heterocyclic rings having 1 hetero atom such as a pyran ring, a 2H-pyran ring, a pyridine ring and a piperidine ring; 6-membered heterocyclic rings having 2 hetero atoms such as a thiopyrane ring, a pyridazine ring, a pyrimidine ring, a pyrazine ring, a piperazine ring and a morpholine ring; 6-membered heterocyclic rings having 3 hetero atoms such as a 1,2,4-triazine ring.

The polycyclic heterocyclic ring includes a bicyclic heterocyclic ring and a tricyclic heterocyclic ring, wherein 2 to 3 monocyclic heterocyclic rings are condensed with each other, or wherein a monocyclic heterocyclic ring is condensed with 1 to 2 aromatic rings such as a benzene ring and a naphthalene ring.

Specific examples of the bicyclic heterocyclic ring include, for example, heterocyclic rings having 1 hetero atom such as a benzofuran ring, an isobenzofuran ring, a 1-benzothiophene ring, a 2-benzothiophene ring, an indole ring, an 3-indole ring, an isoindole ring, an indolizine ring, an indoline ring, an isoindoline ring, a 2H-chromene ring, a chroman ring, an isochroman ring, a 1H-2-benzopyran ring, a quinoline ring, an isoquinoline ring and a 4H-quinolizine ring; heterocyclic rings having 2 hetero atoms such as a benzoimidazole ring, a benzothiazole ring, an 1H-indazole ring, a 1,8-naphthyridine ring, a quinoxaline ring, a quinazoline ring, a quinazolidine ring, a cinnoline ring and a phthalazine ring; heterocyclic rings having four hetero atoms such as a purine ring and a pteridine ring.

Specific examples of the tricyclic heterocyclic ring include, for example, heterocyclic rings having 1 hetero atom such as a carbazole ring, a 4aH-carbazole ring, a xanthene ring, a phenanthridine ring and an acridine ring; heterocyclic rings having 2 hetero atoms such as a β-carboline ring, a perimidine ring, a 1,7-phenanthroline ring, a 1,10-phenanthroline ring, a thianthrene ring, a phenoxathiin ring, a phenoxazine ring, a phenothiazine ring and a phenazine ring.

The substituent of the above heterocyclic ring which may have a substituent includes, for example, a halogen atom, a hydroxyl group, a mercapto group, an oxo group, a thioxo group, a carboxyl group, a sulfo group, a sulfino group, a sulfeno group, a phosphino group, a phosphinoyl group, a formyl group, an amino group, a cyano group and a nitro group; and the above substituent may have further a substituent including, for example, an alkyl group, an alkenyl group, an aryl group, an aralkyl group, an alkoxy group, an aryloxy group, an alkylthio group, an arylthio group, an alkylsulfonyl group, an arylsulfonyl group, an alkylsulfinyl group, an arylsulfinyl group, an alkylphosphino group, an arylphosphino group, an alkylphosphinoyl group, an arylphosphinoyl group, an alkylamino group, an arylamino group, an alkoxycarbonyl group, an aryloxycarbonyl group, an alkoxysulfonyl group, an aryloxysulfonyl group, an acyl group, an acyloxy group, a sulfonyl group and a sulfonyloxy group.

The above alkyl group may be straight chained, branched or cyclic, and includes one generally having 1 to 20, preferably 1 to 15, more preferably 1 to 10 and further preferably 1 to 6 carbon atoms, which is specifically exemplified by a methyl group, an ethyl group, a n-propyl group, an isopropyl group, a n-butyl group, an isobutyl group, a sec-butyl group, a tert-butyl group, a n-pentyl group, an isopentyl group, a sec-pentyl group, a tert-pentyl group, a neopentyl group, a n-hexyl group, an isohexyl group, a sec-hexyl group, a tert-hexyl group, a neohexyl group, a 3-methylpentyl group, a 2-methylpentyl group, a 1,2-dimethylbutyl group, a n-heptyl group, an isoheptyl group, a sec-heptyl group, a tert-heptyl group, a neoheptyl group, an n-octyl group, an isooctyl group, a sec-octyl group, a tert-octyl group, a neooctyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an icosyl group, a cyclopropyl group, a cyclopentyl group, a cyclohexyl group, a cycloheptyl group, a cyclooctyl group, a cyclononyl group, a cyclodecyl group, a cyclododecyl group, a cycloundecyl group, a cyclotridecyl group, a cyclotetradecyl group, a cyclopentadecyl group, a cyclohexadecyl group, a cycloheptadecyl group, a cyclooctadecyl group, a cyclononadecyl group and a cycloicosyl group.

The alkenyl group may be straight chained, branched or cyclic, and includes one generally having 2 to 20, preferably 2 to 10 and more preferably 2 to 6 carbon atoms, and having not less than 1 carbon-carbon double bond in the chain of an alkyl group having not less than 2 carbon atoms among the above alkyl groups, which is specifically exemplified by a vinyl group, an allyl group, a 1-propenyl group, an isopropenyl group, a 3-butenyl group, a 2-butenyl group, a 1-butenyl group, a 1,3-butadienyl group, a 4-pentenyl group, a 3-pentenyl group, a 2-pentenyl group, a 1-pentenyl group, a 1,3-pentadienyl group, a 2,4-pentadienyl group, a 1,1-dimethyl-2-propenyl group, an 1-ethyl-2-propenyl group, a 1,2-dimethyl-1-propenyl group, a 1-methyl-1-butenyl group, a 5-hexenyl group, a 4-hexenyl group, a 2-hexenyl group, a 1-hexenyl group, a 1-methyl-1-hexenyl group, a 2-methyl-2-hexenyl group, a 3-methyl-1,3-hexadienyl group, a 1-heptenyl group, an 2-octenyl group, a 3-nonenyl group, a 4-decenyl group, a 1-dodecenyl group, a 1-tetradecenyl group, a 1-hexadecenyl group, an 1-octadecenyl group, an 1-icosenyl group, a 1-cyclopropenyl group, a 2-cyclopentenyl group, a 2,4-cyclopentadienyl group, a 1-cyclohexenyl group, a 2-cyclohexenyl group, a 3-cyclohexenyl group, a 2-cycloheptenyl group, a 2-cyclononenyl group, a 3-cyclodecenyl group, a 2-cyclotridecenyl group, a 1-cyclohexadecenyl group, a 1-cyclooctadecenyl group and a 1-cycloicosenyl group.

The aryl group includes one generally having 6 to 14, preferably 6 to 10 carbon atoms, which is specifically exemplified by a phenyl group, a naphthyl group and an anthryl group.

The aralkyl group may be straight chained, branched or cyclic, and includes one generally having 7 to 34, preferably 7 to 20 and more preferably 7 to 15 carbon atoms, wherein a hydrogen atom in the above alkyl group is replaced by the above aryl group, which is specifically exemplified by a benzyl group, a phenylethyl group, a phenylpropyl group, a phenylbutyl group, a phenylpentyl group, a phenylhexyl group, a phenylheptyl group, a phenyloctyl group, a phenylnonyl group, a phenyldecyl group, a phenyldodecyl group, a phenylundecyl group, a phenyltridecyl group, a phenyltetradecyl group, a phenylpentadecyl group, a phenylhexadecyl group, a phenylheptadecyl group, a phenyloctadecyl group, a phenylnonadecyl group, a phenylicosyl group, a naphthylethyl group, a naphthylpropyl group, a naphthylbutyl group, a naphthylpentyl group, a naphthylhexyl group, a naphthylheptyl group, a naphthyloctyl group, a naphthylnonyl group, a naphthyldecyl group, a naphthyldodecyl group, a naphthylundecyl group, a naphthyltridecyl group, a naphthyltetradecyl group, a naphthylpentadecyl group, a naphthylhexadecyl group, a naphthylheptadecyl group, a naphthyloctadecyl group, a naphthylnonadecyl group, a naphthylicosyl group, an anthrylethyl group, an anthrylpropyl group, an anthrylbutyl group, an anthrylpentyl group, an anthrylhexyl group, an anthrylheptyl group, an anthryloctyl group, an anthrylnonyl group, an anthryldecyl group, an anthryldodecyl group, an anthrylundecyl group, an anthryltridecyl group, an anthryltetradecyl group, an anthrylpentadecyl group, an anthrylhexadecyl group, an anthrylheptadecyl group, an anthryloctadecyl group, an anthrylnonadecyl group, an anthrylicosyl group, a phenanthrylethyl group, a phenanthrylpropyl group, a phenanthrylbutyl group, a phenanthrylpentyl group, a phenanthrylhexyl group, a phenanthrylheptyl group, a phenanthryloctyl group, a phenanthrylnonyl group, a phenanthryldecyl group, a phenanthryldodecyl group, a phenanthrylundecyl group, a phenanthryltridecyl group, a phenanthryltetradecyl group, a phenanthrylpentadecyl group, a phenanthrylhexadecyl group, a phenanthrylheptadecyl group, a phenanthryloctadecyl group, a phenanthrylnonadecyl group and a phenanthrylicosyl group.

The alkoxy group may be straight chained, branched or cyclic, and includes one generally having 1 to 20, preferably 1 to 15, more preferably 1 to 10 and further preferably 1 to 6 carbon atoms, which is specifically exemplified by a methoxy group, an ethoxy group, a n-propoxy group, an isopropoxy group, a n-butoxy group, an isobutoxy group, a sec-butoxy group, a tert-butoxy group, a n-pentyloxy group, an isopentyloxy group, a sec-pentyloxy group, a tert-pentyloxy group, a neopentyloxy group, a n-hexyloxy group, an isohexyloxy group, a sec-hexyloxy group, a tert-hexyloxy group, a neohexyloxy group, a heptyloxy group, an octyloxy group, a nonyloxy group, a decyloxy group, an undecyloxy group, a tridecyloxy group, a tetradecyloxy group, a pentadecyloxy group, a hexadecyloxy group, a heptadecyloxy group, an octadecyloxy group, a nonadecyloxy group, an icosyloxy group, a cyclohexyloxy group, a cyclooctyloxy group, a cyclodecyloxy group and a cyclononadecyloxy group.

The aryloxy group includes one generally having 6 to 14, preferably 6 to 10 carbon atoms, which is specifically exemplified by a phenoxy group, a naphthyloxy group and an anthryloxy group.

The alkylthio group may be straight chained, branched or cyclic, and includes one generally having 1 to 20, preferably 1 to 15, more preferably 1 to 10 and further preferably 1 to 6 carbon atoms, wherein an oxygen atom in the above alkoxy group is replaced by a sulfur atom, which is specifically exemplified by a methylthio group, an ethylthio group, a n-propylthio group, an isopropylthio group, a n-butylthio group, an isobutylthio group, a sec-butylthio, a tert-butylthio group, a n-pentylthio group, an isopentylthio group, a sec-pentylthio group, a tert-pentylthio group, a neopentylthio group, a n-hexylthio group, an isohexylthio group, a sec-hexylthio group, a tert-hexylthio group, a neohexylthio group, a heptylthio group, an octylthio group, a nonylthio group, a decylthio group, an undecylthio group, a dodecylthio group, a tridecylthio group, a tetradecylthio group, a pentadecylthio group, a hexadecylthio group, a heptadecylthio group, an octadecylthio group, a nonadecylthio group, an icosylthio group, a cyclohexylthio group, a cyclodecylthio group and a cycloheptadecylthio group.

The arylthio group includes one wherein an alkyl group in the above alkylthio group is replaced by the above aryl group, which is specifically exemplified by a phenylthio group, a naphthylthio group and an anthrylthio group.

The alkylsulfonyl group may be straight chained, branched or cyclic, and includes one generally having 1 to 20, preferably 1 to 15, more preferably 1 to 10 and further preferably 1 to 6 carbon atoms, which is specifically exemplified by a methylsulfonyl group, an ethylsulfonyl group, a n-propylsulfonyl group, an isopropylsulfonyl group, a n-butylsulfonyl group, an isobutylsulfonyl group, a sec-butylsulfonyl group, a tert-butylsulfonyl group, a n-pentylsulfonyl group, an isopentylsulfonyl group, a sec-pentylsulfonyl group, a tert-pentylsulfonyl group, a neopentylsulfonyl group, a hexylsulfonyl group, an isohexylsulfonyl group, a sec-hexylsulfonyl group, a tert-hexylsulfonyl group, a neohexylsulfonyl group, a heptylsulfonyl group, an octylsulfonyl group, a nonylsulfonyl group, a decylsulfonyl group, an undecylsulfonyl group, a tetradecylsulfonyl group, a hexadecylsulfonyl group, a heptadecylsulfonyl group, a nonadecylsulfonyl group, an icosylsulfonyl group, a cyclohexylsulfonyl group, a cyclooctylsulfonyl group, a cyclodecylsulfonyl group and a cyclononadecylsulfonyl group.

The arylsulfonyl group includes one generally having 6 to 14, preferably 6 to 10 carbon atoms, which is specifically exemplified by a phenylsulfonyl group, a naphthylsulfonyl group and an anthrylsulfonyl group.

The alkylsulfinyl group may be straight chained, branched or cyclic, and includes one generally having 1 to 20, preferably 1 to 15, more preferably 1 to 10 and further preferably 1 to 6 carbon atoms, which is specifically exemplified by a methylsulfinyl group, an ethylsulfinyl group, a n-propylsulfinyl group, an isopropylsulfinyl group, a n-butylsulfinyl group, an isobutylsulfinyl group, a sec-butylsulfinyl group, a tert-butylsulfinyl group, a n-pentylsulfinyl group, an isopentylsulfinyl group, a sec-pentylsulfinyl group, a tert-pentylsulfinyl group, a neopentylsulfinyl group, a n-hexylsulfinyl group, an isohexylsulfinyl group, a sec-hexylsulfinyl group, a tert-hexylsulfinyl group, a neohexylsulfinyl group, a heptylsulfinyl group, an octylsulfinyl group, a nonylsulfinyl group, a decylsulfinyl group, an undecylsulfinyl group, a dodecylsulfinyl group, a tridecylsulfinyl group, a tetradecylsulfinyl group, a pentadecylsulfinyl group, a hexadecylsulfinyl group, a heptadecylsulfinyl group, an octadecylsulfinyl group, a nonadecylsulfinyl group, an icosylsulfinyl group, a cyclohexylsulfinyl group, a cyclooctylsulfinyl group, a cyclodecylsulfinyl group and a cyclononadecylsulfinyl group.

The arylsulfinyl group includes one, wherein the alkyl group in the above alkylsulfinyl group is replaced by the above aryl group, which is specifically exemplified by a phenylsulfinyl group, a naphthylsulfinyl group and an anthrylsulfinyl group.

The alkylphosphino group includes one, wherein one or two of hydrogen atoms of a phosphino group are each independently replaced by the above alkyl group, which is specifically exemplified by a methylphosphino group, an ethylphosphino group, a n-propylphosphino group, an isopropylphosphino group, a n-butylphosphino group, an isobutylphosphino group, a sec-butylphosphino group, a tert-butylphosphino group, a pentylphosphino group, a hexylphosphino group, a heptylphosphino group, an octylphosphino group, a nonylphosphino group, a decylphosphino group, an undecylphosphino group, a dodecylphosphino group, a tridecylphosphino group, a tetradecylphosphino group, a pentadecylphosphino group, a hexadecylphosphino group, a heptadecylphosphino group, an octadecylphosphino group, a nonadecylphosphino group, an icosylphosphino group, a cyclopentylphosphino group, a cyclohexylphosphino group, a cycloheptylphosphino group, a dimethylphosphino group, an ethylmethylphosphino group, a diethylphosphino group, a methylpropylphosphino group, a dipropylphosphino group, an ethylhexylphosphino group, a dibutylphosphino group, a heptylmethylphosphino group, a methyloctylphosphino group, a decylmethylphosphino group, a dodecylethylphosphino group, a methylpentadecylphosphino group, an ethyloctadecylphosphino group, a cyclopentylmethylphosphino group, a cyclohexylmethylphosphino group, a cyclohexylethylphosphino group, a cyclohexylpropylphosphino group, a cyclohexylbutylphosphino group and a dicyclohexylphosphino group.

The arylphosphino group includes one, wherein one or two of hydrogen atoms of a phosphino group are each replaced by the above aryl group, which is specifically exemplified by a phenylphosphino group, a diphenylphosphino group, a naphthylphosphino group and an anthrylphosphino group.

The alkylphosphinoyl group includes one, wherein one or two of hydrogen atoms of a phosphinoyl group are each independently replaced by the above alkyl group, which is specifically exemplified by a methylphosphinoyl group, an ethylphosphinoyl group, a n-propylphosphinoyl group, an isopropylphosphinoyl group, a n-butylphosphinoyl group, an isobutylphosphinoyl group, a sec-butylphosphinoyl group, a tert-butylphosphinoyl group, a pentylphosphinoyl group, a hexylphosphinoyl group, a heptylphosphinoyl group, an octylphosphinoyl group, a nonylphosphinoyl group, a decylphosphinoyl group, an undecylphosphinoyl group, a dodecylphosphinoyl group, a tridecylphosphinoyl group, a tetradecylphosphinoyl group, a pentadecylphosphinoyl group, a hexadecylphosphinoyl group, a heptadecylphosphinoyl group, an octadecylphosphinoyl group, a nonadecylphosphinoyl group, an icosylphosphinoyl group, a cyclopentylphosphinoyl group, a cyclohexylphosphinoyl group, a cycloheptylphosphinoyl group, a dimethylphosphinoyl group, an ethylmethylphosphinoyl group, a diethylphosphinoyl group, a methylpropylphosphinoyl group, a dipropylphosphinoyl group, an ethylhexylphosphinoyl group, a dibutylphosphinoyl group, a heptylmethylphosphinoyl group, a methyloctylphosphinoyl group, a decylmethylphosphinoyl group, a dodecylethylphosphinoyl group, a methylpentadecylphosphinoyl group, an ethyloctadecylphosphinoyl group, a cyclopentylmethylphosphinoyl group, a cyclohexylmethylphosphinoyl group, a cyclohexylethylphosphinoyl group, a cyclohexylpropylphosphinoyl group, a cyclohexylbutylphosphinoyl group and a dicyclohexylphosphinoyl group.

The arylphosphinoyl group includes one, wherein one or two of hydrogen atoms of a phosphinoyl group are replaced by the above aryl group, which is specifically exemplified by a phenylphosphinoyl group, a diphenylphosphinoyl group, a naphthylphosphinoyl group and an anthrylphosphinoyl group.

The alkylamino group includes one, wherein one or two of hydrogen atoms of an amino group are each independently replaced by the above alkyl group, which is specifically exemplified by a methylamino group, an ethylamino group, a n-propylamino group, an isopropylamino group, a n-butylamino group, an isobutylamino group, a sec-butylamino group, a tert-butylamino group, a pentylamino group, a hexylamino group, a heptylamino group, an octylamino group, a nonylamino group, a decylamino group, an undecylamino group, a dodecylamino group, a tridecylamino group, a tetradecylamino group, a pentadecylamino group, a hexadecylamino group, a heptadecylamino group, an octadecylamino group, a nonadecylamino group, an icosylamino group, a cyclopentylamino group, a cyclohexylamino group, a cycloheptylamino group, a dimethylamino group, an ethylmethylamino group, a diethylamino group, a methylpropylamino group, a dipropylamino group, an ethylhexylamino group, a dibutylamino group, a heptylmethylamino group, a methyloctylamino group, a decylmethylamino group, a dodecylethylamino group, a methylpentadecylamino group, an ethyloctadecylamino group, a cyclopentylmethylamino group, a cyclohexylmethylamino group, a cyclohexylethylamino group, a cyclohexylpropylamino group, a cyclohexylbutylamino group and a dicyclohexylamino group.

The arylamino group includes one, wherein one or two of hydrogen atoms of an amino group are replaced by the above aryl group, which is specifically exemplified by a phenylamino group, a diphenylamino group, a naphthylamino group and an anthrylamino group.

The alkoxycarbonyl group may be straight chained, branched or cyclic, and includes one generally having 2 to 21, preferably 2 to 15, more preferably 2 to 10 and further preferably 2 to 6 carbon atoms, and having further a carbonyl group bonded to an oxygen atom of the above alkoxy group, which is specifically exemplified by a methoxycarbonyl group, an ethoxycarbonyl group, a n-propoxycarbonyl group, an isopropoxycarbonyl group, a n-butoxycarbonyl group, an isobutoxycarbonyl group, a sec-butoxycarbonyl group, a tert-butoxycarbonyl group, a n-pentyloxycarbonyl group, an isopentyloxycarbonyl group, a sec-pentyloxycarbonyl group, a tert-pentyloxycarbonyl group, a neopentyloxycarbonyl group, a hexyloxycarbonyl group, a cyclohexyloxycarbonyl group, a heptyloxycarbonyl group, a cycloheptyloxycarbonyl group, an octyloxycarbonyl group, a nonyloxycarbonyl group, a decyloxycarbonyl group, a cyclodecyloxycarbonyl group, an undecyloxycarbonyl group, a tridecyloxycarbonyl group, a tetradecyloxycarbonyl group, a pentadecyloxycarbonyl group, a hexadecyloxycarbonyl group, a heptadecyloxycarbonyl group, a cycloheptadecyloxycarbonyl group, an octadecyloxycarbonyl group, a nonadecyloxycarbonyl group, an icosyloxycarbonyl group, a cyclopentyloxycarbonyl group, a cyclohexyloxycarbonyl group and a cyclooctyloxycarbonyl group.

The aryloxycarbonyl group includes one generally having 7 to 15, preferably 7 to 11 carbon atoms, which is specifically exemplified by a phenyloxycarbonyl group, a naphthyloxycarbonyl group and an anthryloxycarbonyl group.

The alkoxysulfonyl group may be straight chained, branched or cyclic, and includes one generally having 2 to 21, preferably 2 to 15, more preferably 2 to 10 and further preferably 2 to 6 carbon atoms, having further a sulfonyl group bonded to an oxygen atom of the above alkoxy group, which is specifically exemplified by a methoxysulfonyl group, an ethoxysulfonyl group, a n-propoxysulfonyl group, an isopropoxysulfonyl group, a n-butoxysulfonyl group, an isobutoxysulfonyl group, a sec-butoxysulfonyl group, a tert-butoxysulfonyl group, a n-pentyloxysulfonyl group, an isopentyloxysulfonyl group, a sec-pentyloxysulfonyl group, a tert-pentyloxysulfonyl group, a neopentyloxysulfonyl group, a hexyloxysulfonyl group, a cyclohexyloxysulfonyl group, a heptyloxysulfonyl group, a cycloheptyloxysulfonyl group, an octyloxysulfonyl group, a nonyloxysulfonyl group, a decyloxysulfonyl group, a cyclodecyloxysulfonyl group, an undecyloxysulfonyl group, a dodecyloxysulfonyl group, a tridecyloxysulfonyl group, a tetradecyloxysulfonyl group, a pentadecyloxysulfonyl group, a hexadecyloxysulfonyl group, a heptadecyloxysulfonyl group, a cycloheptadecyloxysulfonyl group, an octadecyloxysulfonyl group, a nonadecyloxysulfonyl group, an icosyloxysulfonyl group, a cyclopentyloxysulfonyl group, a cyclooctyloxysulfonyl group and a cycloheptadecyloxysulfonyl group.

The aryloxysulfonyl group includes one generally having 7 to 15, preferably 7 to 11 carbon atoms, which is specifically exemplified by a phenyloxysulfonyl group, a naphthyloxysulfonyl group and an anthryloxysulfonyl group.

The acyl group includes one derived from an aliphatic carboxylic acid and an aromatic carboxylic acid.

The acyl group derived from an aliphatic carboxylic acid may be straight chained, branched or cyclic, and may also have a double bond in the chain, and includes one generally having 2 to 20, preferably 2 to 15, more preferably 2 to 10 and further preferably 2 to 6 carbon atoms, which is specifically exemplified by an acetyl group, a propionyl group, a butyryl group, an isobutyryl group, a valeryl group, an isovaleryl group, a pivaloyl group, a hexanoyl group, a heptanoyl group, an octanoyl group, a decanoyl group, a lauroyl group, a myristoyl group, a palmitoyl group, a stearoyl group, an icosanoyl group, an acryloyl group, a methacryloyl group, a crotonoyl group and an oleoyl group.

The acyl group derived from an aromatic carboxylic acid includes one generally having 7 to 15, preferably 7 to 11 carbon atoms, which is specifically exemplified by a benzoyl group, a naphthoyl group and an anthroyl group.

The acyloxy group includes an acyloxy group derived from a carboxylic acid having further an —O— bonded to the above acyl group derived from a carboxylic acid, which is exemplified by an acyloxy group derived from an aliphatic carboxylic acid and an aromatic carboxylic acid.

The acyloxy group derived from an aliphatic carboxylic acid may be straight chained, branched or cyclic and may have further a double bond in the chain, and includes one generally having 2 to 20, preferably 2 to 15, more preferably 2 to 10 and further preferably 2 to 6 carbon atoms, which is specifically exemplified by an acetyloxy group, a propionyloxy group, a butyryloxy group, an isobutyryloxy group, a valeryloxy group, an isovaleryloxy group, a pivaloyloxy group, a hexanoyloxy group, a heptanoyloxy group, an octanoyloxy group, a decanoyloxy group, a lauroyloxy group, a myristoyloxy group, a palmitoyloxy group, a stearoyloxy group, an icosanoyloxy group, an acryloyloxy group, a methacryloyloxy group, a crotonoyloxy group, an oleoyloxy group, a cyclohexanoyloxy group and a cyclodecanoyloxy group.

The acyloxy group derived from an aromatic carboxylic acid includes one generally having 7 to 15, preferably 7 to 11 carbon atoms, which is specifically exemplified by a benzoyloxy group, a naphthoyloxy group and an anthroyloxy group.

The sulfonyl group includes one derived from an aliphatic sulfonic acid and an aromatic sulfonic acid.

The sulfonyl group derived from an aliphatic sulfonic acid may be straight chained, branched or cyclic, and includes one generally having 1 to 20, preferably 1 to 15, more preferably 1 to 10 and further preferably 1 to 6 carbon atoms, which is specifically exemplified by a methylsulfonyl group, an ethylsulfonyl group, a n-propylsulfonyl group, an isopropylsulfonyl group, a n-butylsulfonyl group, an isobutylsulfonyl group, a sec-butylsulfonyl group, a tert-butylsulfonyl group, a pentylsulfonyl group, a hexylsulfonyl group, a heptylsulfonyl group, an octylsulfonyl group, a nonylsulfonyl group, a decylsulfonyl group, an undecylsulfonyl group, a dodecylsulfonyl group, s tridecylsulfonyl group, a tetradecylsulfonyl group, a pentadecylsulfonyl group, a hexadecylsulfonyl group, a heptadecylsulfonyl group, an octadecylsulfonyl group, a nonadecylsulfonyl group, an icosylsulfonyl group, a cyclohexylsulfonyl group and a cyclodecylsulfonyl group.

The sulfonyl group derived from an aromatic sulfonic acid includes one generally having 6 to 14, preferably 6 to 10 carbon atoms, which is specifically exemplified by a phenylsulfonyl group, a naphthylsulfonyl group and an anthrylsulfonyl group.

The sulfonyloxy group includes one derived from a sulfonic acid having further an —O— bonded to the above sulfonyl group derived from a sulfonyl acid, which is exemplified by a sulfonyloxy group derived from an aliphatic sulfonic acid and an aromatic sulfonic acid.

The sulfonyloxy group derived from an aliphatic sulfonic acid may be straight chained, branched or cyclic, and includes one generally having 1 to 20, preferably 1 to 15, more preferably 1 to 10 and further preferably 1 to 6 carbon atoms, which is specifically exemplified by a methylsulfonyloxy group, an ethylsulfonyloxy group, a n-propylsulfonyloxy group, an isopropylsulfonyloxy group, a n-butylsulfonyloxy group, an isobutylsulfonyloxy group, a sec-butylsulfonyloxy group, a tert-butylsulfonyloxy group, a pentylsulfonyloxy group, a hexylsulfonyloxy group, a heptylsulfonyloxy group, an octylsulfonyloxy group, a nonylsulfonyloxy group, a decylsulfonyloxy group, an undecylsulfonyloxy group, a dodecylsulfonyloxy group, a tridecylsulfonyloxy group, a tetradecylsulfonyloxy group, a pentadecylsulfonyloxy group, a hexadecylsulfonyloxy group, a heptadecylsulfonyloxy group, an octadecylsulfonyloxy group, a nonadecylsulfonyloxy group, an icosylsulfonyloxy group, a cyclopentylsulfonyloxy group and a cyclohexylsulfonyl group.

The sulfonyloxy group derived from an aromatic sulfonic acid includes one generally having 6 to 14, preferably 6 to 10 carbon atoms, which is specifically exemplified by a phenylsulfonyloxy group, a naphthylsulfonyloxy group and an anthrylsulfonyloxy group.

The halogen atom includes, for example, a chlorine atom, a bromine atom, a fluorine atom and an iodine atom, and among others, a chlorine atom is preferable.

The carboxyl group, the sulfo group, the sulfino group, the sulfeno group, the phosphino group and the phosphinoyl group include also one, wherein a hydrogen atom in these groups is replaced by an alkali metal atom such as sodium, potassium and lithium.

The substituent of a heterocyclic ring which may have a substituent, that is the above alkyl group, alkenyl group, aryl group, aralkyl group, alkoxy group, aryloxy group, alkylthio group, arylthio group, alkylsulfonyl group, arylsulfonyl group, alkylsulfinyl group, arylsulfinyl group, alkylphosphino group, arylphosphino group, alkylphosphinoyl group, arylphosphinoyl group, alkylamino group, arylamino group, alkoxycarbonyl group, aryloxycarbonyl group, alkoxysulfonyl group, aryloxysulfonyl group, acyl group and acyloxy group, may further have a substituent including, for example, an alkyl group, an alkenyl group, an alkynyl group, an aryl group, a hydroxyl group, an alkoxy group, an amino group, an alkylamino group, a mercapto group, an alkylthio group, an formyl group, an acyl group, a carboxyl group, an alkoxycarbonyl group, a carbamoyl group and an alkylcarbamoyl group, and these substituents may be present in number of generally 1 to 6, preferably 1 to 4, more preferably 1 to 2 in the substituent of the aromatic ring.

The substituent of the substituent of a heterocyclic ring, that is an alkyl group, an alkenyl group, an aryl group, an alkoxy group, an alkylamino group, an alkylthio group, an acyl group, a carboxyl group and an alkoxycarbonyl group, includes the same one as the above substituent of a heterocyclic ring.

The alkynyl group as the substituent of the substituent of a heterocyclic ring, may be straight chained, branched or cyclic, and includes one generally having 2 to 20, preferably 2 to 10 and more preferably 2 to 6 carbon atoms, wherein not less than one carbon-carbon triple bond is included in the chain of an alkyl group having not less than two carbon atoms among the above alkyl groups, which is specifically exemplified by an ethenyl group, a 2-propynyl group, a 2-pentynyl group, a 2-nonyl-3-butynyl group, a cyclohexyl-3-ynyl group, a 4-octynyl group and 1-methyldecyl-5-ynyl group.

The alkylcarbamoyl group as the substituent of the substituent of a heterocyclic ring includes one, wherein one or two of hydrogen atoms of a carbamoyl group are each independently replaced by the above alkyl group, which is specifically exemplified by a methylcarbamoyl group, an ethylcarbamoyl group, a n-propylcarbamoyl group, an isopropylcarbamoyl group, a n-butylcarbamoyl group, an isobutylcarbamoyl group, a sec-butylcarbamoyl group, a tert-butylcarbamoyl group, a pentylcarbamoyl group, a hexylcarbamoyl group, a heptylcarbamoyl group, an octylcarbamoyl group, a nonylcarbamoyl group, a decylcarbamoyl group, an undecylcarbamoyl group, a dodecylcarbamoyl group, a tridecylcarbamoyl group, a tetradecylcarbamoyl group, a pentadecylcarbamoyl group, a hexadecylcarbamoyl group, a heptadecylcarbamoyl group, an octadecylcarbamoyl group, a nonadecylcarbamoyl group, an icosylcarbamoyl group, a cyclopentylcarbamoyl group, a cyclohexylcarbamoyl group, a cycloheptylcarbamoyl group, a dimethylcarbamoyl group, an ethylmethylcarbamoyl group, a diethylcarbamoyl group, a methylpropylcarbamoyl group, a dipropylcarbamoyl group, an ethylhexylcarbamoyl group, a dibutylcarbamoyl group, a heptylmethylcarbamoyl group, a methyloctylcarbamoyl group, a decylmethylcarbamoyl group, a dodecylethylcarbamoyl group, a methylpentadecylcarbamoyl group, an ethyloctadecylcarbamoyl group, a cyclopentylmethylcarbamoyl group, a cyclohexylmethylcarbamoyl group, a cyclohexylethyl carbamoyl group, a cyclohexylpropyl carbamoyl group, a cyclohexylbutylcarbamoyl group and a dicyclohexylcarbamoyl group.

The compound having a heterocyclic ring in a deuteration method of the present invention includes, a heterocyclic ring itself, which may have a substituent, as described above, or said heterocyclic ring bound with, for example, sugar chains, various compounds or polymers, and specific examples of the latter include, for example, nucleosides such as adenosine, deoxyadenosine, guanosine, thymidine, uridine, inosine, deoxyguanosine, deoxythymidine and deoxyuridine; and amino acids such as tryptophan.

The compound having an aromatic ring and a heterocyclic ring in a deuteration method of the present invention includes a compound formed by combining as appropriate a compound having the above aromatic ring with a compound having the above heterocyclic ring, and also a compound wherein an aromatic ring and a heterocyclic ring are combined directly by condensation.

A heavy hydrogen source to be reacted with a compound having the above aromatic ring in a deuteration method of the present invention includes, for example, heavy hydrogen gas ($D_2$, $T_2$) and a deuterated solvent.

The deuterated solvent to be used as a heavy hydrogen source includes, in the case where heavy hydrogen is deuterium, for example, heavy water ($D_2O$); deuterated alcohols such as deuterated methanol, deuterated ethanol, deuterated isopropanol, deuterated butanol, deuterated tert-butanol, deuterated pentanol, deuterated hexanol, deuterated heptanol, deuterated octanol, deuterated nonanol, deuterated decanol, deuterated undecanol and deuterated dodecanol; deuterated carboxylic acids such as deuterated formic acid, deuterated acetic acid, deuterated propionic acid, deuterated butyric acid, deuterated isobutyric acid, deuterated valeric acid, deuterated isovaleric acid and deuterated pivalic acid; deuterated ketones such as deuterated acetone, deuterated methyl ethyl ketone, deuterated methyl isobutyl ketone, deuterated diethyl ketone, deuterated dipropyl ketone, deuterated diisopropyl ketone and deuterated dibutyl ketone; organic solvents such as deuterated dimethylsulfoxide; and among others, heavy water and deuterated alcohols are preferable, and heavy water and deuterated methanol are more preferable, and heavy water is particularly preferable in view of environmental aspect or operability. In the case where heavy hydrogen is tritium, the deuterated solvent to be used as a heavy hydrogen source includes, for example, tritium oxide ($T_2O$).

The deuterated solvent may be one wherein at least one hydrogen atom in the molecule is deuterated, and for example, deuterated alcohols wherein at least a hydrogen atom in a hydroxyl group is deuterated, or deuterated carboxylic acids wherein at least a hydrogen atom in a carboxyl group is deuterated, can be used in a method for deuteration of the present invention, and among others, a solvent having a higher deuteration ratio of the hydrogen atoms in the molecule is more preferable, and a solvent wherein all hydrogen atoms in the molecule are deuterated is particularly preferable.

As an amount of a heavy hydrogen source to be used increases, deuteration of the present invention tends to proceed further. In view of cost, however, an amount of heavy hydrogen atoms contained in the heavy hydrogen source is such level, as lower limit, of preferably in the order of not less than equimolar, 10 molar times, 20 molar times, 30 molar times and 40 molar times, and as upper limit, of preferably in the order of 250 molar times and 150 molar times, based on hydrogen atoms deuteratable in a compound having an aromatic ring and/or a heterocyclic ring as a reaction substrate.

A reaction solvent may be used as necessary in a deuteration method of the present invention. A reaction solvent is not necessary to use in the case of a liquid reaction substrate even when heavy hydrogen gas is used as a heavy hydrogen source, and also even in the case of a solid reaction substrate when a deuterated solvent is used as a heavy hydrogen source. However, an appropriate reaction solvent is necessary to use in the case of solid reaction substrate when the heavy hydrogen source is heavy hydrogen gas.

The reaction solvent to be used as necessary is preferably a solvent which is not deuterated by heavy hydrogen gas used as a heavy hydrogen source, or a solvent which can be used as it is as a heavy hydrogen source of deuteration of the present invention even if deuterated by heavy hydrogen gas used as a heavy hydrogen source. A reaction solvent which hardly dissolves a substrate can also be used because deuteration of the present invention can be carried out even in a reaction system of suspension, but a solvent which dissolves a substrate is preferable.

When a solvent deuterated with heavy hydrogen gas used as a heavy hydrogen source can not be used as a heavy hydrogen source of deuteration of the present invention any more, it is not preferable to use such a solvent as a reaction solvent because most of the heavy hydrogen gas to be used as a heavy hydrogen source is consumed for deuteration of the solvent instead of for deuteration of the present invention.

The specific example of the reaction solvent to be used as necessary, includes organic solvents which are not deuterated with heavy hydrogen gas, comprising ethers such as dimethyl ether, diethyl ether, diisopropyl ether, ethylmethyl ether, tert-butylmethyl ether, 1,2-dimethoxyethane, oxirane, 1,4-dioxane, dihydropyrane and tetrahydrofuran; aliphatic hydrocarbons such as hexane, heptane, octane, nonane, decane and cyclohexane; and organic solvents which can be used as a heavy hydrogen source of the present invention even if deuterated by heavy hydrogen gas, comprising water; alcohols such as methanol, ethanol, isopropanol, butanol, tert-butanol, pentanol, hexanol, heptanol, octanol, nonanol, decanol, undecanol and dodecanol; carboxylic acids such as formic acid, acetic acid, propionic acid, butyric acid, isobutyric acid, valeric acid, isovaleric acid and pivalic acid; ketones such as acetone, methyl ethyl ketone, methyl isobutyl ketone, diethyl ketone, dipropyl ketone, diisopropyl ketone and dibutyl ketone; and dimethylsulfoxide.

An activated mixed catalyst of not less than two kinds of catalysts selected from among a palladium catalyst, a platinum catalyst, a rhodium catalyst, an iridium catalyst, a ruthenium catalyst, a nickel catalyst and a cobalt catalyst, of the present invention (hereinafter may be abbreviated as an "activated catalyst mixture") means a catalyst formed by activating a mixed catalyst of not less than two kinds of catalysts selected from among a non-activated palladium catalyst, platinum catalyst, rhodium catalyst, iridium catalyst, ruthenium catalyst, nickel catalyst or cobalt catalyst (hereinafter may be abbreviated as a "non-activated catalyst mixture") by contacting with hydrogen gas or heavy hydrogen gas, or a mixed catalyst of not less than two catalysts formed by activating a non-activated palladium catalyst, platinum catalyst, rhodium catalyst, iridium catalyst, ruthenium catalyst, nickel catalyst or cobalt catalyst (hereinafter may be abbreviated each as a "non-activated catalyst") by contacting with hydrogen gas or heavy hydrogen gas.

In a method for deuteration of the present invention, a catalyst or a mixed catalyst formed by activating in advance a non-activated catalyst or mixed catalyst may be used, or a non-activated catalyst or mixed catalyst may be used similarly in the presence of hydrogen gas or heavy hydrogen gas in a deuteration reaction system. A non-activated catalyst and a catalyst activated in advance may be used at the same time in the presence of hydrogen gas or heavy hydrogen gas in a deuteration reaction system.

For hydrogen gas or heavy hydrogen gas to be present in a deuteration reaction system, the hydrogen gas or heavy hydrogen gas may be passed through a reaction solution, or a sealed deuteration reaction system of the present invention may be replaced with the hydrogen gas or heavy hydrogen gas.

As described above, in a catalyst activation method of replacing a sealed deuteration reaction system of the present invention with hydrogen gas or heavy hydrogen gas, an operation for activating a catalyst in advance is not required, which enables deuteration of the present invention to be efficiently carried out.

Because hydrogen gas or heavy hydrogen gas is not required to be present in a deuteration reaction system when a mixed catalyst activated in advance by hydrogen gas or heavy hydrogen gas is used, even a substrate generally liable to be reduced with hydrogen gas or the like can be subjected to deuteration reaction only without any reduction.

In a method for deuteration of the present invention, an activated mixed catalyst includes, preferably a mixed catalyst of not less than two catalysts including an activated palladium catalyst and a mixed catalyst of not less than two catalysts including an activated platinum catalyst, more preferably a mixed catalyst including an activated palladium catalyst and platinum catalyst.

The palladium catalyst includes one having generally 0 to 4, preferably 0 to 2 and more preferably 0 valence of a palladium atom.

The platinum catalyst includes one having generally 0 to 4, preferably 0 to 2 and more preferably 0 valence of a platinum atom.

The rhodium catalyst includes one having generally 0 or 1, preferably 0 valence of a rhodium atom.

The iridium catalyst includes one having generally 0 to 5, preferably 1 to 3 and more preferably 3 valences of an iridium atom.

The ruthenium catalyst includes one having generally 0 to 2, preferably 0 valence of a ruthenium atom.

The nickel catalyst includes one having generally 0 to 2, preferably 0 valence of a nickel atom.

The cobalt catalyst includes one having generally 0 or 1, preferably 1 valence of a cobalt atom.

The above catalyst may be a metal itself of palladium, platinum, rhodium, iridium, ruthenium, nickel or cobalt, oxides, halides or acetates of these metals, one which may have a ligand, or one which may be one of these metals, metal oxides, metal halides, metal acetates or metal complexes supported on various carriers. Hereinafter, a catalyst supported on a carrier may be abbreviated as a "carrier-supported metal catalyst", and a catalyst not supported on a carrier may be abbreviated as a "metal catalyst".

The carrier-supported metal catalyst, that is a mixed catalyst to be used in a method for deuteration of the present invention, includes a mixture of not less than two activated carrier-supported metal catalysts and a catalyst consisting of not less than two activated catalysts supported on the same carrier, which may be particularly referred to as a composite catalyst.

Among catalysts in a method for deuteration of the present invention, a ligand of a metal catalyst which may have a ligand, includes, for example, 1,5-cyclooctadiene (COD), dibenzylideneacetone (DBA), bipyridine (BPY), phenanthroline (PHE), benzonitrile (PhCN), isocyanide (RNC), triethylarsine (As(Et)$_3$), acetylacetonate (acac), pentamethylcyclopentadienyl (Cp*); organic phosphine ligands such as dimethylphenylphosphine (P(CH$_3$)$_2$Ph), diphenylphosphinoferrocene (DPPF), trimethylphosphine (P(CH$_3$)$_3$), triethylphosphine (PEt$_3$), tri-tert-butylphosphine (P$^t$Bu$_3$), tricyclohexylphosphine (PCy$_3$), trimethoxyphosphine (P(OCH$_3$)$_3$), triethoxyphosphine (P(OEt)$_3$), tri-tert-butoxyphosphine (P(O$^t$Bu)$_3$), triphenylphosphine (PPh$_3$), 1,2-bis(diphenylphosphino)ethane (DPPE), triphenoxyphosphine (P(OPh)$_3$) and tri-o-tolylphosphine (P(o-tolyl)$_3$).

Specific examples of the palladium based metal catalyst include, for example, Pd; palladium hydroxide catalysts such as Pd(OH)$_2$; palladium oxide catalysts such as PdO; halogenated palladium catalysts such as PdBr$_2$, PdCl$_2$ and PdI$_2$; palladium acetate catalysts such as palladium acetate (Pd(OAc)$_2$) and palladium trifluoroacetate (Pd(OCOCF$_3$)$_2$); palladium metal complex catalysts which are coordinated with a ligand such as Pd(RNC)$_2$Cl$_2$, Pd(acac)$_2$, diacetate-bis-(triphenylphosphine)palladium [Pd(OAc)$_2$(PPh$_3$)$_2$], Pd(PPh$_3$)$_4$, Pd$_2$(dba)$_3$, Pd(NH$_3$)$_2$Cl$_2$, Pd(CH$_3$CN)$_2$Cl$_2$, dichloro-bis-(benzonitrile)palladium [Pd(PhCN)$_2$Cl$_2$], Pd(dppe)Cl$_2$, Pd(dppf)Cl$_2$, Pd(PCy$_3$)$_2$Cl$_2$, Pd(PPh$_3$)$_2$Cl$_2$, Pd[P(o-tolyl)$_3$]$_2$Cl$_2$, Pd(cod)$_2$Cl$_2$ and Pd(PPh$_3$)(CH$_3$CN)$_2$Cl$_2$.

Specific examples of the platinum based metal catalyst include, for example, Pt; platinum oxide catalysts such as PtO$_2$; halogenated platinum catalysts such as PtCl$_4$, PtCl$_2$ and K$_2$PtCl$_4$; platinum metal complex catalysts which are coordinated with a ligand such as PtCl$_2$(cod), PtCl$_2$(dba), PtCl$_2$(PCy$_3$)$_2$, PtCl$_2$(P(OEt)$_3$)$_2$, PtCl$_2$(P(O$^t$Bu)$_3$)$_2$, PtCl$_2$(bpy), PtCl$_2$(phe), Pt(PPh$_3$)$_4$, Pt(cod)$_2$, Pt(dba)$_2$, Pt(bpy)$_2$ and Pt(phe)$_2$.

Specific examples of the rhodium based metal catalyst include, for example, Rh and rhodium metal complex catalysts which are coordinated with a ligand such as RhCl(PPh$_3$)$_3$.

Specific examples of the iridium based metal catalyst include, for example, Ir and iridium metal complex catalysts which are coordinated with a ligand such as Ir(cod)(acac) and Cp*Ir(P(CH$_3$)$_3$)IrCl$_2$.

Specific examples of the ruthenium based metal catalyst include, for example, Ru and ruthenium metal complex catalysts which are coordinated with a ligand such as RuCl$_2$(PPh$_3$)$_3$.

Specific examples of the nickel based metal catalyst include, for example, Ni; nickel oxide catalysts such as NiO; halogenated nickel catalysts such as NiCl$_2$; nickel metal complex catalysts which are coordinated with a ligand such as NiCl$_2$(dppe), NiCl$_2$(PPh$_3$)$_2$, Ni(PPh$_3$)$_4$, Ni(P(OPh)$_3$)$_4$ and Ni(cod)$_2$.

Specific examples of the cobalt based metal catalyst include, for example, cobalt metal complex catalysts which are coordinated with a ligand such as Co(C$_3$H$_5$){P(OCH$_3$)$_3$}$_3$.

A carrier, in the case where the above catalyst is supported on a carrier, includes, for example, carbon, alumina, silica gel, zeolite, molecular sieve, ion-exchange resins and polymers, and among others, carbon is preferable.

The ion exchange resin used as a carrier may be one having no adverse effect on deuteration of the present invention, and includes, for example, a cation exchange resin and an anion exchange resin.

The cation exchange resin includes, for example, a weak acidic cation exchange resin and strong acidic cation exchange resin. The anion exchange resin includes, for example, a weak basic anion exchange resin and a strong basic anion exchange resin.

The ion exchange resin generally contains a polymer cross-linked with a bifunctional monomer as a skeleton polymer, to which an acidic group or a basic group is bonded and then is exchanged by various cations or anions (a counter ion), respectively.

Specific examples of the weak acidic cation exchange resin include, for example, one obtained by hydrolysis of a polymer of acrylate ester or a methacrylate ester, cross-linked with divinylbenzene.

Specific examples of the strong acidic cation exchange resin include, for example, one obtained by sulfonation of a copolymer of styrene-divinylbenzene.

Specific examples of the strong basic anion exchange resin include, for example, one wherein an amino group is bonded to an aromatic ring of a copolymer of stylene-divinylbenzene.

Strength of basicity of a basic anion exchange resin increases with an amino group bonded in the order of a primary amino group, a secondary amino group, a tertiary amino group and a quaternary ammonium salt.

An ion exchange resin generally available on the market as well as the above ion exchange resin may be used as a carrier of a catalyst to be used for deuteration of the present invention.

The polymer used as a carrier is not especially limited unless it has adverse effects on deuteration of the present invention, however, an example of such a polymer includes one obtained by polymerization or copolymerization of a monomer shown by following general formula [1]:

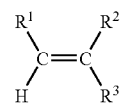

[1]

(wherein R$^1$ is a hydrogen atom, a lower alkyl group, a carboxyl group, a carboxyalkyl group, an alkoxycarbonyl group, a hydroxyalkoxycarbonyl group, a cyano group or a formyl group; R$^2$ is a hydrogen atom, a lower alkyl group, a carboxyl group, an alkoxycarbonyl group, a hydroxyalkoxycarbonyl group, a cyano group or a halogen atom; R$^3$ is a hydrogen atom, a lower alkyl group, a haloalkyl group, a hydroxyl group, an aryl group which may have a substituent, an aliphatic heterocyclic group, an aromatic heterocyclic group, a halogen atom, an alkoxycarbonyl group, a hydroxyalkoxycarbonyl group, a sulfo group, a cyano group, a cyano-containing alkyl group, an acyloxy group, a carboxyl group, a carboxyalkyl group, an aldehyde group, an amino group, an aminoalkyl group, a carbamoyl group, a N-alkylcarbamoyl group or a hydroxyalkyl group, and $R^1$ and $R^2$ may form an alicyclic ring together with the adjacent —C=C— bond).

In general formula [1], the lower alkyl group shown by $R^1$ to $R^3$ may be straight chained, branched or cyclic, and includes an alkyl group having 1 to 6 carbon atoms, which is specifically exemplified by a methyl group, an ethyl group, a n-propyl group, an isopropyl group, a n-butyl group, an isobutyl group, a tert-butyl group, a sec-butyl group, a n-pentyl group, an isopentyl group, a tert-pentyl group, a 1-methylpentyl group, a n-hexyl group, an isohexyl group, a cyclopropyl group, a cyclopentyl group and a cyclohexyl group.

The carboxyalkyl group shown by $R^1$ and $R^2$ includes one, wherein part of hydrogen atoms of the above lower alkyl group are replaced by a carboxyl group, which is specifically exemplified by a carboxymethyl group, a carboxyethyl group, a carboxypropyl group, a carboxybutyl group, a carboxypentyl group and a carboxyhexyl group.

The alkoxycarbonyl group shown by $R^1$ to $R^3$ includes preferably one having 2 to 11 carbon atoms, which is specifically exemplified by a methoxycarbonyl group, an ethoxycarbonyl group, a propoxycarbonyl group, a butoxycarbonyl group, a pentyloxycarbonyl group, a hexyloxycarbonyl group, a heptyloxycarbonyl group, a 2-ethylhexyloxycarbonyl group, an octyloxycarbonyl group, a nonyloxycarbonyl group and a decyloxycarbonyl group.

The hydroxyalkoxycarbonyl group shown by $R^1$ to $R^3$ includes one, wherein part of hydrogen atoms of the above alkoxycarbonyl group having 2 to 11 carbon atoms are replaced by a hydroxyl group, which is specifically exemplified by a hydroxymethyloxycarbonyl group, a hydroxyethyloxycarbonyl group, a hydroxypropyloxycarbonyl group, a hydroxybutyloxycarbonyl group, a hydroxypentyloxycarbonyl group, a hydroxyhexyloxycarbonyl group, a hydroxyheptyloxycarbonyl group, a hydroxyoctyloxycarbonyl group, a hydroxynonyloxycarbonyl group and a hydroxydecyloxycarbonyl group.

The halogen atom shown by $R^2$ and $R^3$ includes, for example, fluorine, chlorine, bromine and iodine.

The haloalkyl group shown by $R^3$ includes one having 1 to 6 carbon atoms, wherein the above lower alkyl group shown by $R^1$ to $R^3$ is halogenated (for example, fluorinated, chlorinated, brominated and iodinated), which is specifically exemplified by a chloromethyl group, a bromomethyl group, a trifluoromethyl group, a 2-chloroethyl group, a 3-chloropropyl group, a 3-bromopropyl group, a 3,3,3-trifluoropropyl group, a 4-chlorobutyl group, a 5-chloropentyl group and a 6-chlorohexyl group.

The aryl group of the aryl group which may have a substituent includes, for example, a phenyl group, a tolyl group, a xylyl group and a naphthyl group, and said substituent includes, for example, an amino group, a hydroxyl group, a lower alkoxy group and a carboxyl group. Specific examples of the substituted aryl group include, for example, an aminophenyl group, a toluidino group, a hydroxyphenyl group, a methoxyphenyl group, a tert-butoxyphenyl group and a carboxyphenyl group.

The aliphatic heterocyclic group includes preferably a 5- or 6-membered one having 1 to 3 hetero atoms such as a nitrogen atom, an oxygen atom and a sulfur atom, which is specifically exemplified by a 2-oxopyrrolidyl group, a piperidyl group, a piperidino group, a piperazinyl group and a morpholino group.

The aromatic heterocyclic group includes preferably a 5- or 6-membered one having 1 to 3 hetero atoms such as a nitrogen atom, an oxygen atom and a sulfur atom, which is specifically exemplified by a pyridyl group, an imidazolyl group, a thiazolyl group, a furyl group and a pyranyl group.

The cyano-containing alkyl group includes one, wherein part of hydrogen atoms of the above lower alkyl group are replaced by a cyano group, which is specifically exemplified by a cyanomethyl group, a 2-cyanoethyl group, a 2-cyanopropyl group, a 3-cyanopropyl group, a 2-cyanobutyl group, a 4-cyanobutyl group, a 5-cyanopentyl group and a 6-cyanohexyl group.

The acyloxy group includes one derived from a carboxylic acid having 2 to 20 carbon atoms, which is specifically exemplified by an acetyloxy group, a propionyloxy group, a butyryloxy group, a pentanoyloxy group, a nonanoyloxy group, a decanoyloxy group and a benzoyloxy group.

The aminoalkyl group includes one, wherein part of hydrogen atoms of the above lower alkyl group are replaced by an amino group, which is specifically exemplified by an aminomethyl group, an aminoethyl group, an aminopropyl group, an aminobutyl group, an aminopentyl group and an aminohexyl group.

The N-alkylcarbamoyl group includes one, wherein part of hydrogen atoms of a carbamoyl group are replaced by an alkyl group, which is specifically exemplified by an N-methylcarbamoyl group, an N-ethylcarbamoyl group, an N-n-propylcarbamoyl group, an N-isopropylcarbamoyl group, an N-n-butylcarbamoyl group and an N-tert-butylcarbamoyl group.

The hydroxyalkyl group includes one, wherein part of hydrogen atoms of the above lower alkyl group are replaced by a hydroxyl group, which is specifically exemplified by a hydroxymethyl group, a hydroxyethyl group, a hydroxypropyl group, a hydroxybutyl group, a hydroxypentyl group and a hydroxyhexyl group.

The alicyclic ring in the case where $R^1$ and $R^2$ are bonded together with the adjacent —C=C— bond to form an alicyclic ring, includes an unsaturated alicyclic ring having 5 to 10 carbon atoms, and may be monocyclic or polycyclic, which is specifically exemplified by a norbornene ring, a cyclopentene ring, a cyclohexene ring, a cyclooctene ring and a cyclodecene ring.

The specific examples of the monomer shown by general formula [1] include ethylenically unsaturated aliphatic hydrocarbons having 2 to 20 carbon atoms such as ethylene, propylene, butylene and isobutylene; ethylenically unsaturated aromatic hydrocarbons having 8 to 20 carbon atoms such as styrene, 4-methylstyrene, 4-ethylstyrene and divinylbenzene; alkenyl esters having 3 to 20 carbon atoms such as vinyl formate, vinyl acetate, vinyl propionate and isopropenyl acetate; halogen-containing ethylenically unsaturated compounds having 2 to 20 carbon atoms such as vinyl chloride, vinylidene chloride, vinylidene fluoride and tetrafluoroethylene; ethylenically unsaturated carboxylic acids having 3 to 20 carbon atoms such as acrylic acid, methacrylic acid, itaconic acid, maleic acid, fumaric acid, crotonic acid, vinyl acetic acid, allylacetic acid and vinylbenzoic acid (these acids may form an alkali metal salt such as sodium and potassium, or an ammonium salt); ethylenically unsaturated carboxylic esters such as methyl methacrylate, ethyl methacrylate, propyl methacrylate, butyl methacrylate, 2-ethylhexyl methacrylate, methyl acrylate, ethyl acrylate, propyl acrylate, butyl acrylate, 2-ethylhexyl acrylate, lauryl methacrylate, stearyl acrylate, methyl itaconate, ethyl itaconate, methyl maleate, ethyl maleate, methyl fumarate, ethyl fumarate, methyl crotonate, ethyl crotonate and methyl 3-butenoate; cyano-containing ethylenically unsaturated compounds having 3 to 20 carbon atoms such as acrylonitrile, methacrylonitrile and allyl cyanide; ethylenically unsaturated amide compounds having 3 to 20 carbon atoms such as acrylamide and methacrylamide; ethylenically unsaturated aldehydes having 3 to 20 carbon atoms such as acrolein and crotonaldehyde; ethylenically unsaturated sulfonic acids having 2 to 20 carbon atoms such as vinylsulfonic acid and 4-vinylbenzene sulfonic acid (these acids may form an alkali metal salts such as sodium and potassium); ethylenically unsaturated aliphatic amines having 2 to 20 carbon atoms such as vinylamine and allylamine; ethylenically unsaturated aromatic amines having 8 to 20 carbon atoms such as vinylaniline; ethylenically unsaturated aliphatic heterocyclic amines having 5 to 20 carbon atoms such as N-vinylpyrrolidone and vinylpiperidine; ethylenically unsaturated alcohols having 3 to 20 carbon atoms such as allyl alcohol and crotyl alcohol; ethylenically unsaturated phenols having 8 to 20 carbon atoms such as 4-vinylphenol, etc.

When the above polymers and the like are used as a carrier, a carrier which is hardly deuterated itself by deuteration of the present invention is preferably used. However, a catalyst supported on a deuterable carrier itself can also be used for deuteration of the present invention.

In the carrier-supported catalyst, content of the catalyst metal, that is palladium, platinum, rhodium, iridium, ruthenium, nickel and cobalt, is generally 1 to 99% by weight, preferably 1 to 50% by weight, more preferably 1 to 30% by weight, further more preferably 1 to 20% by weight, and particularly preferably 5 to 10% by weight based on the whole catalyst.

In a method for deuteration of the present invention, among the above carrier-supported metal catalysts, a mixed catalyst containing palladium carbon, palladium hydroxide carbon or platinum carbon is preferably used. Among the above catalysts, a mixed catalyst containing palladium carbon or platinum carbon is more preferable and a mixed catalyst containing both of palladium carbon and platinum carbon is particularly preferable.

Mixing ratio in a mixed catalyst in the present invention is not limited, but is preferably 1:99 to 99:1, more preferably 1:9 to 9:1. Deuteration using the above mixed catalyst gives a higher deuteration ratio than that deuteration using a single catalyst.

When a mixed catalyst of a palladium catalyst and a platinum catalyst, for example, is used, the mixing ratio may be generally 1:99 to 99:1, preferably 1:9 to 9:1 based on the amount of the metal. When a mixed catalyst of palladium carbon and platinum carbon, for example, is used, the mixing ratio may be generally 1:99 to 99:1, preferably 1:9 to 9:1, more preferably 1:5 to 5:1, further more preferably 1:2 to 2:1 and particularly preferably 1:1 based on the weight of the palladium metal of the palladium carbon and the platinum metal of the platinum carbon.

In a method for deuteration of the present invention, amount of an activated mixed catalyst or non-activated mixed catalyst to be used is generally so-called the catalyst quantity, preferably in the order of, 0.01 to 200% by weight, 0.01 to 100% by weight, 0.01 to 50% by weight, 0.01 to 20% by weight, 0.1 to 20% by weight, 1 to 20% by weight and 10 to 20% by weight based on a compound having an aromatic ring and/or a heterocyclic ring to be used as a reaction substrate, irrespective of whether the mixed catalyst is supported by a carrier or not, and upper limit content of the catalyst metal in said whole catalyst is preferably in the order of, 20% by weight, 10% by weight, 5% by weight and 2% by weight, while lower limit content is preferably in the order of, 0.0005% by weight, 0.005% by weight, 0.05% by weight and 0.5% by weight.

In the case when a non-activated mixed catalyst is used in a reaction of the present invention, amount of hydrogen gas to be used when the hydrogen gas is present in a reaction system to activate a non-activated mixed catalyst may be a little more than the necessary amount to activate the catalyst to efficiently carry out activation of the catalyst, though there is possibility that an excessive amount of hydrogen gas shows adverse effect on a deuteration reaction of the present invention such as hydrogenation of a deuterated solvent as a heavy hydrogen source. Such amount of hydrogen gas is generally 1 to 20,000 equivalents and preferably 10 to 700 equivalents based on the catalyst.

Amount of heavy hydrogen to be used when the heavy hydrogen is present in a reaction system to activate a non-activated mixed catalyst may be the necessary amount to activate the catalyst, generally 1 to 20,000 equivalents and preferably 10 to 700 equivalents based on the catalyst. However, even if amount of said heavy hydrogen is excessively large, deuteration of the present invention can be performed without any problem, because said heavy hydrogen is in contact with a deuterated solvent in the reaction system and has effect to further deuterate said solvent.

In a method for deuteration of the present invention, the lower limit of reaction temperature is generally 10° C., preferably in the order of 20° C., 40° C., 60° C., 80° C., 140° C. and 160° C., and the upper limit thereof is generally 300° C., preferably in the order of 200° C. and 180° C.

In order to obtain a higher temperature in a reaction vessel than the boiling point of a solvent, it is enough to keep the reaction vessel sealed and heat and/or pressurize, resulting in getting the system under pressure.

To pressurize a reaction system, hydrogen gas or heavy hydrogen gas for activating a catalyst may be used, but an inert gas such as nitrogen gas and argon gas may be used in addition.

Reaction time in a method for deuteration of the present invention is generally 30 minutes to 100 hours, preferably 1 to 50 hours, more preferably 1 to 30 hours and further more preferably 3 to 30 hours.

A method for deuteration of the present invention will be described by taking, as an example, the case to use heavy water as a heavy hydrogen source and use a mixed catalyst of a non-activated palladium catalyst and platinum catalyst.

For example, a compound (substrate) having an aromatic ring and/or a heterocyclic ring and a mixed catalyst (1:1) of a palladium catalyst and a platinum catalyst of 0.01 to 200% by weight based on said substrate (the total amount of the palladium metal and the platinum metal is 0.0005 to 20% by weight based on the substrate) are added to a deuterated solvent (1 to 20,000 equivalents, preferably 10 to 700 equivalents based on the mixed catalyst), followed by sealing the reaction system, replacing the atmosphere in the reaction system with hydrogen gas and reacting under stirring in an oil bath at about 20 to 200° C. for about 30 minutes to 100 hours. After completion of the reaction, the mixed catalyst is filtered off from the reaction solution, the filtrate is purified and then subjected to structural analysis by $^1$H-NMR, $^2$H-NMR and mass spectrum measurements.

When a product is hardly soluble in a deuterated solvent, isolation of the product from the reaction solution may be carried out according to known purification methods such as extraction of the product from the reaction solution using an organic solvent in which the product is soluble and then filtering off a mixed catalyst.

By performing a method for deuteration of the present invention using a mixed catalyst activated in advance as an activated mixed catalyst and a deuterated solvent as a heavy hydrogen source, even when a compound having an aromatic ring and/or a heterocyclic ring contains a halogen atom as a substituent, only the aromatic ring and/or the heterocyclic ring can be deuterated without the above halogen atom being substituted with a hydrogen atom or a deuterium atom, or even when a compound having an aromatic ring and/or a heterocyclic ring contains a substituent such as a nitro group and a cyano group, only the aromatic ring and/or the heterocyclic ring can be deuterated without the above substituents being reduced.

As described above, according to a method of the present invention by which a compound having an aromatic ring and/or a heterocyclic ring is deuterated in a deuterated solvent in the presence of an activated mixed catalyst, it is deuterate very efficiently a hydrogen atom at the position conventionally having a relatively low deuteration ratio among hydrogen atoms of a compound having an aromatic ring and/or a heterocyclic ring.

In more detail, in the case of conventional deuteration of a compound having an aromatic ring using the sole catalyst such as a palladium catalyst and a platinum catalyst, the deuteration ratio of a hydrogen atom bonded to a carbon atom in an aromatic ring adjacent to a substituent bonded to the aromatic ring (hereinafter, may be abbreviated as hydrogen atom at the ortho position) is lower compared with that of a hydrogen atom bonded to a carbon atom at the benzyl position, and the deuteration ratio of a hydrogen atom bonded to a carbon atom located apart from the benzyl position also tends to get lower as the carbon atom is located farther from the benzyl position. In contrast, an extremely high deuteration ratio can be obtained, even for a compound having a hydrogen atom at said positions, by carrying out a deuteration reaction of the present invention using a mixed catalyst of not less than two kinds of catalysts selected from among a palladium catalyst, a platinum catalyst, a rhodium catalyst, an iridium catalyst, a ruthenium catalyst, a nickel catalyst and a cobalt catalyst.

The deuteration ratio of a hydrogen atom at the ortho position in a compound having an aromatic ring is remarkably higher in many cases when an activated mixed catalyst of a palladium catalyst and a platinum catalyst is used for deuteration than when an activated palladium catalyst alone and an activated platinum catalyst alone are each used for deuteration, which shows a synergic effect of using a mixed catalyst.

The deuteration ratio of a hydrogen atom bonded to a carbon atom in a heterocyclic ring adjacent to the carbon atom to which a substituent is bonded is also remarkably higher in many cases when an activated mixed catalyst of a palladium catalyst and a platinum catalyst is used for deuteration than when an activated palladium catalyst alone and an activated platinum catalyst alone are each used for deuteration, which shows a synergic effect of using a mixed catalyst.

Furthermore, a hydrogen atom of an alkylamino group bonded to an aromatic ring or a heterocyclic ring can also be deuterated efficiently by a method for deuteration of the present invention.

In the following, the present invention is described in more detail referring to Examples, but the present invention is not limited thereto by any means. In the following Examples, palladium carbon having a palladium metal content of 10% by weight and platinum carbon having a platinum metal content of 5% by weight were used.

EXAMPLE

Example 1

In 17 mL of heavy water ($D_2O$) were suspended 500 mg of 5-phenylvaleric acid, 50 mg of palladium carbon and 100 mg of platinum carbon, followed by replacing the atmosphere of a sealed reaction system with hydrogen gas and conducting a reaction in an oil bath at 180° C. for about 24 hours. After completion of the reaction, the reaction solution was extracted with ether, followed by filtering off the catalyst. The filtrate was concentrated under reduced pressure and subjected to structural analysis by measuring $^1$H-NMR, $^2$H-NMR and mass spectrum. The deuteration ratios of the hydrogen atoms of the reaction substrate are shown in Table 1. Each deuteration ratio in Table 1 indicates the deuteration ratio of a hydrogen atom at a position numbered in the structural formula of the reaction substrate.

Comparative Example 1-1

A similar deuteration reaction as in Example 1 was conducted except for using 50 mg of palladium carbon as a catalyst. The results are also shown in Table 1.

Comparative Example 1-2

A similar deuteration reaction as in Example 1 was conducted except for using 100 mg of platinum carbon as a catalyst. The results are also shown in Table 1.

Comparative Example 1-3

A similar deuteration reaction as in Example 1 was conducted except for using 500 mg of the 5-phenylvaleric acid deuterated in above Comparative Example 1-2 as a reaction substrate and 50 mg of palladium carbon as a catalyst. The results are also shown in Table 1.

TABLE 1

| | Catalyst | Amount of metal (mg) Pd | Amount of metal (mg) Pt | Reaction substrate | Deuteration ratio (%) |
|---|---|---|---|---|---|
| Example 1 | Pd/C + Pt/C | 5 | 5 | (2)(3)(4) phenyl-COOH structure with positions (1)(1)(1)(2)(2) on ring and (4)(5) on chain | (1)(2)(3)(4):97 (5):94 |
| Comparative Example 1-1 | Pd/C | 5 | — | | (1)(2):15 (3)(4):97, (5):95 |
| Comparative Example 1-2 | Pt/C | — | 5 | | (1):97, (2):19 (3):28, (4):8, (5):10 |
| Comparative Example 1-3 | Pt/C → Pd/C | 5 | 5 | | (1):97, (2):30 (3)(4)(5):97 |

Example 2

A similar deuteration reaction as in Example 1 was conducted except for using 500 mg of 5-phenylbutyric acid instead of 5-phenylvaleric acid as a reaction substrate. The results are shown in Table 2.

Comparative Example 2-1

A similar deuteration reaction as in Example 2 was conducted except for using 50 mg of palladium carbon as a catalyst. The results are also shown in Table 2.

Comparative Example 2-2

A similar deuteration reaction as in Example 2 was conducted except for using 100 mg of platinum carbon as a catalyst. The results are also shown in Table 2.

Example 4

A similar deuteration reaction as in Example 1 was conducted except for using 500 mg of 2-n-propylphenol instead of 5-phenylvaleric acid as a reaction substrate. The results are shown in Table 4.

Comparative Example 4-1

A similar deuteration reaction as in Example 4 was conducted except for using 50 mg of palladium carbon as a catalyst. The results are also shown in Table 4.

TABLE 2

|  | Catalyst | Amount of metal (mg) Pd | Pt | Reaction substrate | Deuteration ratio (%) |
| --- | --- | --- | --- | --- | --- |
| Example 2 | Pd/C + Pt/C | 5 | 5 | 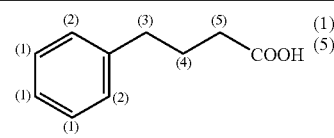 | (1)(2):97, (3)(4):98 (5):97 |
| Comparative Example 2-1 | Pd/C | 5 | — |  | (1)(2):25 (3)(4)(5):100 |
| Comparative Example 2-2 | Pt/C | — | 5 |  | (1):96, (2):74, (3):70 (4):28, (5):20 |

Example 3

A similar deuteration reaction as in Example 1 was conducted except for using 500 mg of 4-n-propylbenzoic acid instead of 5-phenylvaleric acid as a reaction substrate. The results are shown in Table 3.

Comparative Example 3-1

A similar deuteration reaction as in Example 3 was conducted except for using 50 mg of palladium carbon as a catalyst. The results are also shown in Table 3.

Comparative Example 3-2

A similar deuteration reaction as in Example 3 was conducted except for using 100 mg of platinum carbon as a catalyst. The results are also shown in Table 3.

Comparative Example 4-2

A similar deuteration reaction as in Example 4 was conducted except for using 100 mg of palladium carbon as a catalyst. The results are also shown in Table 4.

Comparative Example 4-3

A similar deuteration reaction as in Example 4 was conducted except for using 100 mg of platinum carbon as a catalyst. The results are also shown in Table 4.

TABLE 3

|  | Catalyst | Amount of metal (mg) Pd | Pt | Reaction substrate | Deuteration ratio (%) |
| --- | --- | --- | --- | --- | --- |
| Example 3 | Pd/C + Pt/C | 5 | 5 | 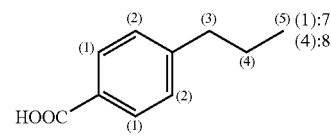 | (1):78, (2):58, (3):90 (4):83, (5):77 |
| Comparative Example 3-1 | Pd/C | 5 | — |  | (1):3, (2):4, (3):96 (4):93, (5):92 |
| Comparative Example 3-2 | Pt/C | — | 5 |  | (1):62, (2):17, (3):15 (4):12, (5):11 |

TABLE 4

| | Catalyst | Amount of metal (mg) Pd | Amount of metal (mg) Pt | Reaction substrate | Deuteration ratio (%) |
|---|---|---|---|---|---|
| Example 4 | Pd/C + Pt/C | 5 | 5 | 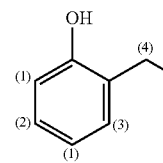 | (1)(2)(4)(5)(6):97, (3):87 |
| Comparative Example 4-1 | Pd/C | 5 | — | | (1):99, (2)(4):98, (3):48, (5)(6):97 |
| Comparative Example 4-2 | Pd/C | 10 | — | | (1)(4)(6):97, (2):98, (3):54, (5):98 |
| Comparative Example 4-3 | Pt/C | — | 5 | | (1)(2):98, (3):38, (4):72, (5):42, (6):28 |

Example 5

A similar deuteration reaction as in Example 1 was conducted except for using 500 mg of 4-n-propylphenol instead of 5-phenylvaleric acid as a reaction substrate. The results are shown in Table 5.

Comparative Example 5-1

A similar deuteration reaction as in Example 5 was conducted except for using 50 mg of palladium carbon as a catalyst. The results are also shown in Table 5.

Comparative Example 5-2

A similar deuteration reaction as in Example 5 was conducted except for using 100 mg of platinum carbon as a catalyst. The results are also shown in Table 5.

Example 6

A similar deuteration reaction as in Example 1 was conducted except for using 500 mg of 2-n-propylaniline instead of 5-phenylvaleric acid as a reaction substrate. The results are shown in Table 6.

Comparative Example 6-1

A similar deuteration reaction as in Example 6 was conducted except for using 50 mg of palladium carbon as a catalyst. The results are also shown in Table 6.

Comparative Example 6-2

A similar deuteration reaction as in Example 6 was conducted except for using 100 mg of platinum carbon as a catalyst. The results are also shown in Table 6.

TABLE 5

| | Catalyst | Amount of metal (mg) Pd | Amount of metal (mg) Pt | Reaction substrate | Deuteration ratio (%) |
|---|---|---|---|---|---|
| Example 5 | Pd/C + Pt/C | 5 | 5 | 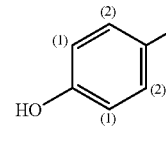 | (1)(5):97, (2):93, (3)(4):98 |
| Comparative Example 5-1 | Pd/C | 5 | — | | (1):97, (2):46 (3)(4)(5):98 |
| Comparative Example 5-2 | Pt/C | — | 5 | | (1):97, (2)(4):19, (3):27, (5):14 |

TABLE 6

| | Catalyst | Amount of metal (mg) Pd | Pt | Reaction substrate | Deuteration ratio (%) |
|---|---|---|---|---|---|
| Example 6 | Pd/C + Pt/C | 5 | 5 | 2-aminophenyl ethyl group (positions (1)-(7), NH$_2$ at (5)) | (1)(3):99, (2):97, (4):59, (5)(6):97, (7):94 |
| Comparative Example 6-1 | Pd/C | 5 | — | | (1)(2):96, (3):97, (4):12, (5)(6)(7):97 |
| Comparative Example 6-2 | Pt/C | — | 5 | | (1)(2):97, (3):98, (4):14, (5):49, (6):32, (7):20 |

Example 7

A similar deuteration reaction as in Example 1 was conducted except for using 500 mg of 4-n-propylaniline instead of 5-phenylvaleric acid as a reaction substrate. The results are shown in Table 7.

Comparative Example 7-1

A similar deuteration reaction as in Example 7 was conducted except for using 50 mg of palladium carbon as a catalyst. The results are also shown in Table 7.

Comparative Example 7-2

A similar deuteration reaction as in Example 7 was conducted except for using 100 mg of platinum carbon as a catalyst. The results are also shown in Table 7.

Example 8

A similar deuteration reaction as in Example 1 was conducted except for using 500 mg of N,N-dimethylaniline instead of 5-phenylvaleric acid as a reaction substrate. The results are shown in Table 8.

Comparative Example 8-1

A similar deuteration reaction as in Example 8 was conducted except for using 50 mg of palladium carbon as a catalyst. The results are also shown in Table 8.

Comparative Example 8-2

A similar deuteration reaction as in Example 8 was conducted except for using 100 mg of platinum carbon as a catalyst. The results are also shown in Table 8.

TABLE 7

| | Catalyst | Amount of metal (mg) Pd | Pt | Reaction substrate | Deuteration ratio (%) |
|---|---|---|---|---|---|
| Example 7 | Pd/C + Pt/C | 5 | 5 | 4-n-propylaniline (H$_2$N-phenyl-CH$_2$CH$_2$CH$_3$) | (1)(2)(3)(4)(5):97 |
| Comparative Example 7-1 | Pd/C | 5 | — | | (1):98, (2):16, (3)(4):99, (5):98 |
| Comparative Example 7-2 | Pt/C | — | 5 | | (1):97, (2):87, (3):97, (4):73, (5):34 |

TABLE 8

| Catalyst | Amount of metal (mg) Pd | Pt | Reaction substrate | Deuteration ratio (%) |
|---|---|---|---|---|
| Example 8 | Pd/C + Pt/C | 5 | 5 | (4) H$_3$C, CH$_3$ (4) N (3) (3) (2) (2) (1) | (1)(3):98, (2):34, (4):98 |
| Comparative Example 8-1 | Pd/C | 5 | — | | (1)(3):98, (2):21, (4):51 |
| Comparative Example 8-2 | Pt/C | — | 5 | | (1)(3):98, (2):81, (4):54 |

Example 9

A similar deuteration reaction as in Example 1 was conducted except for using 500 mg of nicotinic acid instead of 5-phenylvaleric acid as a reaction substrate. The results are shown in Table 9.

Comparative Example 9-1

A similar deuteration reaction as in Example 9 was conducted except for using 50 mg of palladium carbon as a catalyst. The results are also shown in Table 9.

Comparative Example 9-2

A similar deuteration reaction as in Example 9 was conducted except for using 100 mg of platinum carbon as a catalyst. The results are also shown in Table 9.

TABLE 9

| Catalyst | Amount of metal (mg) Pd | Pt | Reaction substrate | Deuteration ratio (%) |
|---|---|---|---|---|
| Example 9 | Pd/C + Pt/C | 5 | 5 | (4) COOH (3) (2) N (1) | (1)(2)(3):99, (4):48 |
| Comparative Example 9-1 | Pd/C | 5 | — | | (1)(3):98, (2):99, (4):10 |
| Comparative Example 9-2 | Pt/C | — | 5 | | (1):54, (2):99, (3):65, (4):11 |

Example 10

A similar deuteration reaction as in Example 1 was conducted except for using 500 mg of 4-dimethylaminopyridine instead of 5-phenylvaleric acid as a reaction substrate. The results are shown in Table 10.

Comparative Example 10-1

A similar deuteration reaction as in Example 10 was conducted except for using 50 mg of palladium carbon as a catalyst. The results are also shown in Table 10.

Comparative Example 10-2

A similar deuteration reaction as in Example 10 was conducted except for using 100 mg of platinum carbon as a catalyst. The results are also shown in Table 10.

TABLE 10

| Catalyst | Amount of metal (mg) Pd | Pt | Reaction substrate | Deuteration ratio (%) |
|---|---|---|---|---|
| Example 10 | Pd/C + Pt/C | 5 | 5 | (3) H$_3$C, CH$_3$ (3) N (2) (2) (1) N (1) | (1):99, (2):16, (3):24 |
| Comparative Example 10-1 | Pd/C | 5 | — | | (1):99, (2):6, (3):3 |
| Comparative Example 10-2 | Pt/C | — | 5 | | (1):100, (2):9, (3):5 |

As is appear from the above Examples, it can be understood that a compound having an aromatic ring and/or a heterocyclic ring can be efficiently deuterated by a method for deuteration of the present invention using a mixed catalyst. Furthermore, as is clear from the comparison between each Example and the Comparative Examples corresponding thereto, it has been found that a mixed catalyst of the present invention can efficiently deuterate a hydrogen atom on an aromatic ring, particularly a hydrogen atom at the ortho position, and a hydrogen atom of an alkylene chain bonded to an aromatic ring, for which the deuteration ratio is low with use of a palladium carbon catalyst alone or a platinum carbon catalyst alone. Further, it can be understood that a synergic effect is obtained by combining two or more catalysts, from the fact that in many cases of deuteration by a method for deuteration of the present invention, a deuteration ratio by a mixed catalyst in Examples is even higher than the sum of a deuteration ratio by a palladium catalyst alone and a deuteration ratio by a platinum catalyst alone in Comparative Examples for a hydrogen atom on an aromatic ring or a heterocyclic ring at the ortho position to a substitute and a hydrogen atom belonging to a substitute such as a dialkylamino group bonded to an aromatic ring or a heterocyclic ring.

INDUSTRIAL APPLICABILITY

A compound having a high deuteration ratio for a hydrogen atom on an aromatic ring or a heterocyclic ring, a hydrogen atom belonging to an alkylene chain bonded to an aromatic ring or a heterocyclic ring and a hydrogen atom belonging to a substituent such as an alkylamino group can be easily obtained by a method for deuteration of the present invention of a compound having an aromatic ring and/or a heterocyclic ring using an activated mixed catalyst of not less than two kinds of catalysts selected from among a palladium catalyst, a platinum catalyst, a rhodium catalyst, an iridium catalyst, a ruthenium catalyst, a nickel catalyst and a cobalt catalyst. Particularly, the method for deuteration of the present invention can deuterate extremely efficiently a hydrogen atom at the ortho position on an aromatic ring to a substitute bonded to the aromatic ring and a hydrogen atom on a heterocyclic ring belonging to the carbon atoms adjacent to the carbon atom bonded to a substituent which are said to be difficult to improve the deuteration ratio thereof by conventional methods.

What is claimed is:

1. A method for deuteration of a compound having a substituted benzene ring, comprising reacting the compound having the substituted benzene ring with a heavy hydrogen source in the presence of an activated mixed catalyst consisting of a palladium catalyst and a platinum catalyst under sealed reflux condition,
    wherein the compound comprises at least one substituent bound to a benzene ring in the compound, and the substituent comprises at least one carbon atom and at least one hydrogen atom, the at least one hydrogen atom being bound to the at least one carbon atom in the substituent, and
    wherein all hydrogen atoms that are bound to carbon atoms and are located in both the at least one substituent and the benzene ring of the compound are deuterated at a weight average deuteration ratio in a range of 74.5% or higher.

2. The method for deuteration according to claim 1, wherein the heavy hydrogen source is a deuterated solvent.

3. The method for deuteration according to claim 2, wherein the deuterated solvent is heavy water ($D_2O$).

4. The method for deuteration according to claim 1, wherein the activated mixed catalyst is a catalyst obtained by activating mixed non-activated catalysts consisting of a palladium catalyst and a platinum catalyst by contacting the non-activated catalysts with hydrogen gas or heavy hydrogen gas.

5. The method for deuteration according to claim 4, wherein the contact of the non-activated mixed catalyst with the hydrogen gas or the heavy hydrogen gas is carried out in a reaction system of the deuteration.

6. The method for deuteration according to claim 1, wherein the palladium catalyst is palladium carbon.

7. The method for deuteration according to claim 1, wherein the platinum catalyst is platinum carbon.

8. The method for deuteration according to claim 1, wherein the activated mixed catalyst of a palladium catalyst and a platinum catalyst has a weight ratio of each metal in the palladium catalyst and the platinum catalyst from 1:5 to 5:1.

9. The method for deuteration according to claim 1, wherein the compound comprises at least one optionally substituted alkyl group as the at least one substituent.

10. The method for deuteration according to claim 1, wherein the compound comprises at least one optionally substituted alkylamino group as the at least one substituent.

11. The method for deuteration according to claim 1, wherein the at least one substituent in the compound is substituted with a carboxyl group.

12. The method for deuteration according to claim 1, wherein the compound comprises at least one optionally substituted alkenyl group as the substituent.

13. The method for deuteration according to claim 1, wherein at least one deuteration ratio of the hydrogen deuterated in the compound is higher than a deuteration ratio of the hydrogen obtained by a method using the palladium catalyst alone and a deuteration ratio of the hydrogen obtained by a method using the platinum catalyst alone.

14. The method for deuteration according to claim 1, wherein the at least one substituent in the compound is at least one group selected from the group consisting of alkyl, alkenyl, aryl, aralkyl, alkoxy, aryloxy, alkylthio, arylthio, alkylsulfonyl, arylsulfonyl, alkylsulfinyl, arylsulfinyl, alkylphosphino, arylphosphino, alkylphosphinoyl, arylphosphinoyl, alkylamino, arylamino, alkoxycarbonyl, aryloxycarbonyl, alkoxysulfonyl, aryloxysulfonyl, acyl, and acyloxy, which are optionally substituted.

15. The method for deuteration according to claim 1, wherein the reacting the compound having the substituted benzene ring with the heavy hydrogen source in the presence of the activated mixed catalyst consisting of the palladium catalyst and the platinum catalyst is performed for a period from 1 to 50 hours.

16. A method for deuteration of a compound having a substituted benzene ring, comprising reacting the compound having the substituted benzene ring with a heavy hydrogen source in the presence of an activated mixed catalyst consisting of a palladium catalyst and a platinum catalyst under sealed reflux condition,
    wherein the compound comprises at least one substituent bound to a benzoic ring in the compound, and the substituent comprises at least one carbon atom and at least one hydrogen atom, the at least one hydrogen atom being bound to the at least one carbon atom in the substituent, and
    hydrogen bound to carbon in an ortho-position of the benzene ring relative to the substituent is deuterated more by the reacting step in the presence of an activated mixed catalyst than the hydrogen in the ortho-position deuterated in the presence of an activated palladium catalyst alone or in the presence of an activated platinum catalyst alone, wherein a weight average deuteration ratio of the hydrogen atoms that are bound to the carbon atoms and are located in both the at least one substituent and the benzene ring of the compound is 74.5% or higher.

17. The method for deuteration according to claim 16, wherein the reacting step is performed for a period from 1 to 50 hours.

* * * * *